(12) United States Patent
Bischof et al.

(10) Patent No.: US 10,183,960 B1
(45) Date of Patent: Jan. 22, 2019

(54) PERFLUOROHYDROCARBYL-N2-PHOSPHINYL AMIDINE COMPOUNDS, CHROMIUM SALT COMPLEXES, CATALYST SYSTEMS, AND THEIR USE TO OLIGOMERIZE ETHYLENE

(71) Applicant: Chevron Phillips Chemical Company LP, The Woodlands, TX (US)

(72) Inventors: Steven M. Bischof, Humble, TX (US); Uriah J. Kilgore, Kingwood, TX (US); Orson L. Sydora, Houston, TX (US); Daniel H. Ess, Provo, UT (US); Jack T. Fuller, III, Los Angeles, CA (US); Doo-Hyun Kwon, Draper, UT (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 15/712,304

(22) Filed: Sep. 22, 2017

(51) Int. Cl.
*C07F 9/6584* (2006.01)
*C07F 11/00* (2006.01)
(Continued)

(52) U.S. Cl.
CPC ............ *C07F 9/65306* (2013.01); *C07C 2/34* (2013.01); *C07F 9/6584* (2013.01); *C07F 11/00* (2013.01); *C08F 10/02* (2013.01); *C08K 5/0091* (2013.01)

(58) Field of Classification Search
CPC ..... C07F 9/65306; C07F 9/6584; C07F 11/00
See application file for complete search history.

(56) References Cited

U.S. PATENT DOCUMENTS

| | | |
|---|---|---|
| 3,361,525 A | 1/1968 | De Rycke et al. |
| 5,217,703 A | 6/1993 | Goodson |

(Continued)

FOREIGN PATENT DOCUMENTS

| | | |
|---|---|---|
| CN | 1490291 A | 4/2004 |
| DE | 1146892 B | 4/1963 |

(Continued)

OTHER PUBLICATIONS

Morse, J. G., et al., "Substituted Difluoro- and Dichlorophosphines," Inorganic Syntheses, 1967, pp. 147-156, vol. 10 McGraw-Hill Book Company, Inc.

(Continued)

*Primary Examiner* — Catherine S Branch
(74) *Attorney, Agent, or Firm* — Conley Rose, P.C.

(57) ABSTRACT

A catalyst system comprising an $N^2$-phosphinylamidine chromium salt complex having Structure PFHNPACr I:

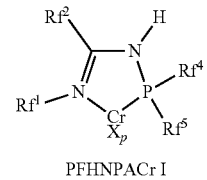

PFHNPACr I wherein $Rf^1$, $Rf^2$, $Rf^4$, and $Rf^5$ are independently selected from a perfluorohydrocarbyl group; and $CrX_p$ is a chromium salt; X is a monoanion, and p is an integer from 2 to 6. A process comprising a) contacting i) ethylene, ii) a catalyst system comprising an $N^2$-phosphinylamidine chromium salt complex having Structure PFHNPACr I:

PFHNPACr I (Continued)

wherein each $Rf^1$, $Rf^2$, $Rf^4$, and $Rf^5$ are independently selected from a perfluorohydrocarbyl group and $CrX_p$ is a chromium salt; X is a monoanion and p is an integer from 2 to 6, and iii) optionally an organic reaction medium; and b) forming an oligomer product in a reaction zone.

24 Claims, 1 Drawing Sheet

(51) Int. Cl.

| | |
|---|---|
| C07F 9/653 | (2006.01) |
| C08F 10/02 | (2006.01) |
| C08K 5/00 | (2006.01) |
| C07C 2/34 | (2006.01) |

(56) References Cited

U.S. PATENT DOCUMENTS

| | | |
|---|---|---|
| 7,276,566 B2 | 10/2007 | Muruganandam et al. |
| 7,300,904 B2 | 11/2007 | Dixon et al. |
| 7,361,623 B2 | 4/2008 | Dixon et al. |
| 7,554,001 B2 | 6/2009 | Dixon et al. |
| 7,994,363 B2 | 8/2011 | Gao et al. |
| 8,252,956 B2 | 8/2012 | Gao et al. |
| 8,367,786 B2 | 2/2013 | Dixon et al. |
| 8,680,003 B2 | 3/2014 | Sydora et al. |
| 8,865,610 B2 | 10/2014 | Sydora et al. |
| 9,283,555 B2 | 3/2016 | Sydora et al. |
| 9,732,106 B2 | 8/2017 | Sydora et al. |
| 2002/0182124 A1 | 12/2002 | Woodard et al. |
| 2006/0247399 A1 | 11/2006 | McConville et al. |
| 2007/0185360 A1 | 8/2007 | Buchanan et al. |
| 2008/0207973 A1 | 8/2008 | Palmas et al. |
| 2010/0041841 A1 | 2/2010 | Terry et al. |
| 2010/0222622 A1 | 9/2010 | Overett et al. |
| 2010/0240847 A1 | 9/2010 | Dixon et al. |
| 2010/0274065 A1 | 10/2010 | Sydora |
| 2012/0142989 A1 | 6/2012 | Jaber et al. |
| 2012/0309965 A1 | 12/2012 | Sydora et al. |
| 2013/0090508 A1 | 4/2013 | Wang et al. |
| 2013/0331629 A1 | 12/2013 | Sydora et al. |
| 2016/0375431 A1 | 12/2016 | Carney et al. |
| 2017/0341998 A1 | 11/2017 | Bischof et al. |
| 2017/0341999 A1 | 11/2017 | Fern et al. |
| 2017/0342000 A1 | 11/2017 | Bischof et al. |
| 2017/0342001 A1 | 11/2017 | Fern et al. |
| 2017/0349505 A1 | 12/2017 | Kilgore et al. |

FOREIGN PATENT DOCUMENTS

| | | |
|---|---|---|
| EP | 0780353 A1 | 6/1997 |
| EP | 2684857 A1 | 1/2014 |
| WO | 0204119 A1 | 1/2002 |
| WO | 2004056477 A1 | 7/2004 |
| WO | 2004056478 A1 | 7/2004 |
| WO | 2004056479 A1 | 7/2004 |
| WO | 2004056480 A1 | 7/2004 |
| WO | 2005039758 A1 | 5/2005 |
| WO | 2005123633 A1 | 12/2005 |
| WO | 2005123884 A2 | 12/2005 |
| WO | 2007007272 A2 | 1/2007 |
| WO | 2007088329 A1 | 8/2007 |
| WO | 2008014139 A2 | 1/2008 |
| WO | 2008119153 A1 | 10/2008 |
| WO | 2010034101 A1 | 4/2010 |
| WO | 2010034102 A1 | 4/2010 |
| WO | 2010051415 A1 | 5/2010 |
| WO | 2011130822 A1 | 10/2011 |
| WO | 2011137027 A1 | 11/2011 |
| WO | 2011140629 A1 | 11/2011 |
| WO | 2012051698 A1 | 4/2012 |
| WO | 2012071644 A1 | 6/2012 |
| WO | 2012092415 A1 | 7/2012 |
| WO | 2012142693 A1 | 10/2012 |
| WO | 2013168106 A1 | 11/2013 |
| WO | 2015094207 A1 | 6/2015 |
| WO | 2015097599 A1 | 7/2015 |
| WO | 2017010998 A1 | 1/2017 |
| WO | 2017011127 A1 | 1/2017 |

OTHER PUBLICATIONS

Singh, Rajendra P., et al., "The first application of SelectfluorTM in electrophilic fluorination of amines: a new route to -NF2, -NHF, and >NF compounds," Chemical Communication, 2001, pp. 1196-1197, vol. 13, Royal Society of Chemistry.
Office Action dated Jun. 28, 2018 (24 pages), U.S. Appl. No. 15/166,991, filed May 27, 2016.
Office Action dated Jun. 25, 2018 (43 pages), U.S. Appl. No. 15/719,107, filed Sep. 28, 2017.
Office Action dated Jul. 17, 2018 (53 pages), U.S. Appl. No. 15/615,113, filed Jun. 6, 2017.
Office Action dated Jul. 27, 2018 (24 pages), U.S. Appl. No. 15/167,017, filed May 27, 2016.
Imhoff, Donald W., et al., "Characterization of Methylaluminoxanes and Determination of Trimethylaluminum Using Proton NMR," Organometallics, 1998, pp. 1941-1945, vol. 17, American Chemical Society.
Office Action dated Aug. 2, 2018 (19 pages), U.S. Appl. No. 15/167,024, filed May 27, 2016.
Office Action (Final) dated Feb. 28, 2018 (43 pages), U.S. Appl. No. 15/167,017, filed May 27, 2016.
Agapie, Theodor, et al., "Mechanistic Studies of Olefin and Alkyne Trimerization with Chromium Catalysts: Deuterium Labeling and Studies of Regiochemistry Using a Model Chromacyclopentane Complex," J. Am. Chem. Soc., 2007, pp. 14281-14295, vol. 129, No. 46, American Chemical Society.
Bollmann, Annette, et al., "Ethylene Tetramerization: A New Route to Produce 1-Octene in Exceptionally High Selectivities,"J. Am. Chem. Soc., 2004, pp. 14712-14713, vol. 126, No. 45, American Chemical Society.
Carter, Anthea, et al., "High activity ethylene trimerisation catalysts based on diphospine ligands," Chemical Communications, vol. 8, 2002, pp. 858-859 plus 2 pages Supplementary Information.
Filing receipt and specification for patent application entitled "Fouling Protection for an Oligomerization Reactor Inlet," by Steven M. Bischof, et al., filed Jun. 6, 2017 as U.S. Appl. No. 15/615,113.
Group notation revised in periodic table, Feb. 4, 1985, C&EN, pp. 26-27.
McNaught, Alan D., et al., "Compendium of Chemical Terminology," IUPAC Recommendations, Second edition, 1997, 5 pages, Wiley-Blackwell.
Sydora, Orson L., et al., "Selective Ethylene Tri-/Tetramerization Catalysts," ACS Catalysis, 2012, pp. 2452-2455, vol. 2, American Chemical Society.
Office Action dated Apr. 25, 2017 (21 pages), U.S. Appl. No. 15/166,991, filed May 27, 2016.
Office Action dated Jul. 24, 2017 (33 pages), U.S. Appl. No. 15/167,009, filed May 27, 2016.
Foreign communication from a related counterpart application—International Search Report and Written Opinion, PCT/US2017/033165, dated Aug. 3, 2017, 11 pages.
Foreign communication from a related counterpart application—International Search Report and Written Opinion, PCT/US2017/033168, dated Aug. 3, 2017, 8 pages.
Office Action dated Aug. 2, 2017 (36 pages), U.S. Appl. No. 15/167,024, filed May 27, 2016.
Foreign communication from a related counterpart application—International Search Report and Written Opinion, PCT/US2017/032191, dated Aug. 14, 2017, 15 pages.
Kuhlmann, S,. et al,. "Chromium catalyzed tetramerization of ethylene in a continuous tube reactor—Proof of concept and kinetic aspects," Journal of Catalysis, 2009, pp. 83-91, vol. 262, No. 1, Elsevier Inc.

(56) References Cited

OTHER PUBLICATIONS

Office Action dated Aug. 30, 2017 (28 pages), U.S. Appl. No. 15/167,017, filed May 27, 2016.
Foreign communication from a related counterpart application—International Search Report and Written Opinion, PCT/US2017/032199, dated Aug. 17, 2017, 14 pages.
Office Action (Final) dated Nov. 1, 2017 (40 pages), U.S. Appl. No. 15/166,991, filed May 27, 2017.
AkzoNobel Product Data Sheet MMAO-3A/Heptane Solutions, 2014, 2 pgs.
AkzoNobel Safety Data Sheet MMAO-3A 7 wt% Al in Heptane, 2016, 17 pgs.
AkzoNobel Product Data Sheet MMAO-20/Heptane Solutions, 2014, 2 pgs.
AkzoNobel Safety Data Sheet MMAO-20 11-30% in Heptane, 2007, 9 pgs.
Kappler, B., et al., "Real-time Monitoring of Ethene/1-hexene Copolymerizations: Determination of Catalyst Activity, Copolymer Composition and Copolymerization Parameters," Polymer, 2003, vol. 44, pp. 6179-6186.
Bartlett, Stuart A., et al., "Activation of [CrCl3{R—Sn(H)S—R}] Catalysts for Selective Trimerization of Ethene: A Freeze-Quench Cr K-Edge XAFS Study," ACS Catalysis, Oct. 21, 2014, pp. 4201-4204, vol. 4, No. 11, American Chemical Society.
Bhaduri, Sumit, et al., "Density functional studies on chromium catalyzed ethylene trimerization," Journal of Organometallic Chemistry, Apr. 15, 2009, pp. 1297-1307, vol. 694, Elsevier B. V.
Britovsek, George, J. P.; "A DFT Mechanistic Study on Ethylene Tri- and Tetramerization with Cr/PNP Catalysts: Single versus Double Insertion Pathways," Chemistry A European Journal, Nov. 14, 2016, pp. 16891-16896, vol. 22, No. 47, Wiley-VCH Verlag GmbH & Co. KGaA, Weinheim.
Britovsek, George, J. P.; "Mechanistic study of ethylene tri- and tetramerisation with Cr/PNP catalysts: effects of additional donors," Catalysis Science & Technology, Oct. 28, 2016, pp. 8234-8241, vol. 6, No. 23, Royal Society of Chemistry.
Budzelaar, Peter H.M., "Ethene trimerization at CrI/CrIII—A Density functional theory (DFT) Study," Canadian Journal of Chemistry, 2009, pp. 832-837, vol. 87, Canadian Journal of Chemistry.
Filing receipt and specification for patent application entitled "Carbonyl-Containing Perfluorohydrocarbyl-N2-Phosphinyl Amidine Compounds, Chromium Salt Complexes and Their Use to Oligomerize Ethylene," by Steven M. Bischof, et al., filed Sep. 22, 2017 as U.S. Appl. No. 15/712,295.
Filing receipt and specification for patent application entitled "Fluorinated N2-Phosphinyl Amidine Compounds, Chromium Salt Complexes, Catalyst Systems, and Their Use to Oligomerize Ethylene," by Steven M. Bischof, et al., filed Sep. 22, 2017 as U.S. Appl. No. 15/712,307.
Gong, Minglan, et al., "Selective Co-Oligomerization of Ethylene and 1-Hexene by Chromium-PNP Catalysts: A DFT Study," Organometallics, Mar. 29, 2016, pp. 972-981, vol. 35, No. 7, American Chemical Society.
Hossain, Anwar, et al., "Spin-crossover in Chromium-catalyzed Ethylene Trimerization" Density Functional Theory Study,"Bulletin of the Korean Chemical Society, Sep. 2014," pp. 2835-2838, vol. 35, No. 9, Korea Chemical Society.
Marenich, Aleksandr V., et al., "Universal Solvation Model Based on Solute Electron Density and on a Continuum Model of the Solvent Defined by the Bulk Dielectric Constant and Atomic Surface Tensions," Journal of Physical Chemistry B, Apr. 14, 2009, pp. 6378-6396, vol. 113, No. 18, American Chemical Society.
Qi, Yuan, et al., "Role of 1,2-Dimethoxyethane in the Transformation from Ethylene Polymerization to Trimerization Using Chromium Tris(2-ethylhexanoate)-Based Catalyst System: A DFT Study," Organometallics, Mar. 2, 2010, pp. 1588-1602, vol. 29, No. 7, American Chemical Society.
Van Rensburg, Werner Janse, et al., "A DFT Study toward the Mechanish of Chromium-Catalyzed Ethylene Trimerization," Organometallics, Feb. 17, 2004, pp. 1207-1222, vol. 23, No. 6, American Chemical Society.
Yang, Yun, et al., "Mechanistic DFT Study on Ethylene Trimerization of Chromium Catalysts Supported by a Versatile Pyrrole Ligand System," Organometallics, May 15, 2014, pp. 2599-2607, vol. 33, No. 10, American Chemical Society.
Fawcett, F.S., et al., "Cyanogen Fluoride: Synthesis and Properties," Journal of the American Chemical Society, Jul. 5, 1964, pp. 2576-2579, vol. 86, No. 13, American Chemical Society.
Office Action (Final) dated Feb. 6, 2018 (43 pages), U.S. Appl. No. 15/167,009, filed May 27, 2016.
Office Action (Final) dated Feb. 6, 2018 (53 pages), U.S. Appl. No. 15/167,024, filed May 27, 2016.
Filing receipt and specification for patent application entitled "Oligomerization Reactions Using Aluminoxanes," by Steven M. Bischof, et al., filed Sep. 28, 2017, 2017 as U.S. Appl. No. 15/719,107.

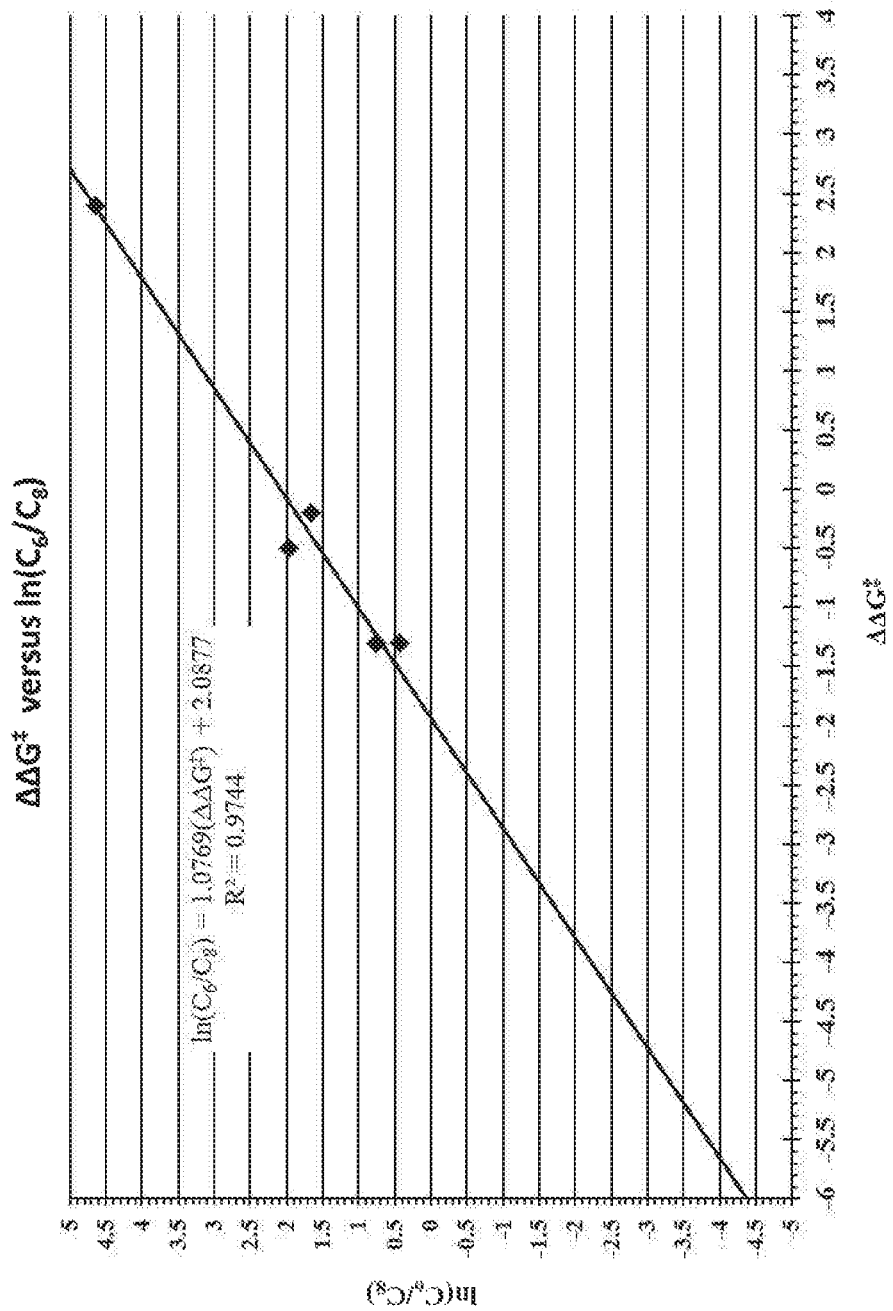

PERFLUOROHYDROCARBYL-N2-PHOSPHINYL AMIDINE COMPOUNDS, CHROMIUM SALT COMPLEXES, CATALYST SYSTEMS, AND THEIR USE TO OLIGOMERIZE ETHYLENE

TECHNICAL FIELD

This disclosure relates to perfluorohydrocarbyl-$N^2$-phosphinyl amidines, perfluorohydrocarbyl-$N^2$-phosphinyl amidine chromium salt complexes and compositions comprising the same. The disclosure also relates to methods of producing the perfluorohydrocarbyl-$N^2$-phosphinyl amidines and the perfluorohydrocarbyl-$N^2$-phosphinyl amidine chromium salt complexes. The disclosure further relates to catalyst systems comprising the perfluorohydrocarbyl-$N^2$-phosphinyl amidine chromium salt complexes and use of the perfluorohydrocarbyl-$N^2$-phosphinyl amidine chromium salt complexes in the oligomerization of ethylene.

BACKGROUND

Olefins, also commonly known as alkenes, are important items of commerce. Their many applications include employment as intermediates in the manufacture of detergents, as precursors to more environmentally friendly refined oils, as monomers, and as precursors for many other types of products. An important subset of olefins is alpha olefins. One method of making alpha olefins is via oligomerization of ethylene, which is a catalytic reaction involving various types of catalysts and/or catalyst systems. Examples of catalysts and catalyst systems used commercially in the oligomerization of ethylene include alkylaluminum compounds, certain nickel-phosphine complexes, a titanium halide with a Lewis acid (e.g., diethyl aluminum chloride), a selective 1-hexene catalyst system containing a chromium containing compound (e.g., a chromium carboxylate), a nitrogen containing ligand (e.g., a pyrrole), a metal alkyl (e.g., alkyl aluminum compounds), and selective trimerization and/or tetramerization catalyst systems using a metal complex of a compound having a diphosphinylaminyl group.

Several non-commercial ethylene oligomerization catalyst systems are based upon metal complexes of pyridine bis-imines, and metal complexes of α-diimine compounds having a metal complexing group. These catalyst systems typically use an alkyl aluminum compound (e.g., aluminoxane) to activate the metal complexes for olefin oligomerization.

Applications and demand for olefins (e.g., alpha olefins) continue to multiply, and competition to supply them correspondingly intensifies. Thus, additional novel and improved catalyst systems and methods for ethylene oligomerization are desirable.

SUMMARY

Disclosed herein is a catalyst system comprising an $N^2$-phosphinylamidine chromium salt complex having Structure PFHNPACr I:

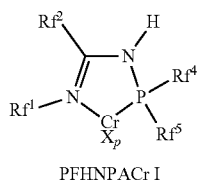

PFHNPACr I wherein $Rf^1$, $Rf^2$, $Rf^4$, and $Rf^5$ are independently selected from a perfluorohydrocarbyl group, wherein $CrX_p$ is a chromium salt wherein X is a monoanion, and wherein p is an integer from 2 to 6.

Also disclosed herein is a process comprising: a) contacting i) ethylene; ii) a catalyst system comprising an $N^2$-phosphinylamidine chromium salt complex having Structure PFHNPACr I wherein each $Rf^1$, $Rf^2$, $Rf^4$, and $Rf^5$ are independently selected from a perfluorohydrocarbyl group and $CrX_p$ is a chromium salt where X is a monoanion and p is an integer from 2 to 6, and iii) optionally an organic reaction medium; and b) forming an oligomer product in a reaction zone.

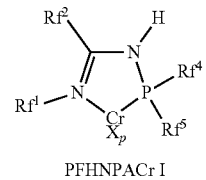

PFHNPACr I

BRIEF DESCRIPTION OF THE DRAWINGS

FIG. 1 is a plot the calculated Gibbs free energy difference, $\Delta\Delta G^{\ddagger}$, between the transition states leading to 1-hexene and 1-octene versus the natural logarithm of the quantity of 1-hexene and 1-octene, versus $\ln(C_6/C_8)$ for five experimentally evaluated ethylene oligomerization using $N^2$-phosphinylamidine chromium salt complex catalyst systems.

DETAILED DESCRIPTION

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology. $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Groups of elements of the periodic table are indicated using the numbering scheme indicated in the version of the periodic table of elements published in *Chemical and Engineering News*, 63(5), 27, 1985. In some instances, a group of elements can be indicated using a common name assigned to the group; for example alkali earth metals (or alkali metals) for Group 1 elements, alkaline earth metals (or alkaline metals) for Group 2 elements, transition metals for Group 3-12 elements, and halogens for Group 17 elements.

Regarding claim transitional terms or phrases, the transitional term "comprising", which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the subject matter described herein. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter the composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms "comprising," "consisting essentially of," and "consisting of" apply only to the feature class which is utilized and it is possible to have different transitional terms or phrases utilized with different features within a claim. For example, a method can comprise several recited steps (and other non-recited steps) but utilize a catalyst system preparation consisting of specific steps; or alternatively, consist of specific steps and/or utilize a catalyst system comprising recited components and other non-recited components.

Within this specification, use of "comprising" or an equivalent expression contemplates the use of the phrase "consisting essentially of," "consists essentially of," or equivalent expressions as alternative embodiments to the open-ended expression. Additionally, use of "comprising" or an equivalent expression or use of "consisting essentially of" in the specification contemplates the use of the phrase "consisting of," "consists of," or equivalent expressions as an alternative to the open-ended expression or middle ground expression, respectively. For example, "comprising" should be understood to include "consisting essentially of," and "consisting of" as alternative embodiments for the aspect, features, and/or elements presented in the specification unless specifically indicated otherwise.

While compositions and methods are described in terms of "comprising" various components or steps, the compositions and methods can also "consist essentially of" or "consist of" the various components or steps.

The terms "a," "an," and "the" are intended, unless specifically indicated otherwise, to include plural alternatives, e.g., at least one. For instance, the disclosure of "a trialkylaluminum compound" is meant to encompass one trialkylaluminum compound, or mixtures or combinations of more than one trialkylaluminum compound unless otherwise specified.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to pentane includes n-pentane, 2-methyl-butane, and 2,2-dimethylpropane while a general reference to a butyl group includes an n-butyl group, a sec-butyl group, an iso-butyl group, and a tert-butyl group. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner. These groups can be utilized as substituents or coordinated or bonded to metal atoms. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") of hydrogen atoms from a parent compound, which in this example can be described as an "alkane group," and which encompasses an "alkyl group," an "alkylene group," and materials having three or more hydrogens atoms, as necessary for the situation, removed from the alkane. Throughout, the disclosure that a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "substituted" when used to describe a group, for example, when referring to a substituted analog of a particular group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

Unless otherwise specified, any carbon-containing group for which the number of carbon atoms is not specified can have, according to proper chemical practice, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, or any range or combination of ranges between these values. For example, unless otherwise specified, any carbon-containing group can have from 1 to 30 carbon atoms, from 1 to 25 carbon atoms, from 1 to 20 carbon atoms, from 1 to 15 carbon atoms, from 1 to 10 carbon atoms, or from 1 to 5 carbon atoms, and the like. Moreover, other identifiers or qualifying terms can be utilized to indicate the presence or absence of a particular substituent, a particular regiochemistry and/or stereochemistry, or the presence or absence of a branched underlying structure or backbone.

An amidine group is a group having the general structure.

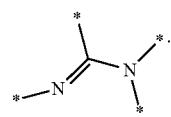

Within the amidine group the nitrogen participating in a double bond with the central carbon atom is referred to as the $N^1$ nitrogen and the nitrogen atom participating in a single bond with the central carbon atom is referred to as the $N^2$ nitrogen. Similarly, the groups attached to the $N^1$ and $N^2$ nitrogen atoms are referred to as the $N^1$ group and $N^2$ group, respectively. An $N^2$-phosphinyl amidine group has the general structure

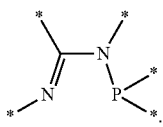

Within the $N^2$-phosphinyl amidine group the $N^1$ and $N^2$ nitrogen atoms and $N^1$ and $N^2$ groups have the same meaning as described for the amidine group. Consequently, an $N^2$-phosphinyl amidine group has the phosphinyl group attached to the $N^2$ nitrogen atom. Within the amidine group and $N^2$-phosphinyl amidine group the carbon atom between the two nitrogen atoms is the central carbon atom and any substituent attached to it is referred to as the central carbon group.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, phosphines, and so forth. An "organyl group," "organylene group," or "organic group" can be aliphatic, inclusive of being cyclic or acyclic, or can be aromatic. "Organyl groups," "organylene groups," and "organic groups" also encompass heteroatom-containing rings, heteroatom-containing ring systems, heteroaromatic rings, and heteroaromatic ring systems. "Organyl groups," "organylene groups," and "organic groups" can be linear or branched unless otherwise specified. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, as members.

For the purposes of this application, the term or variations of the term "organyl group consisting of inert functional groups" refers to an organyl group wherein the organic functional group(s) and/or atom(s) other than carbon and hydrogen present in the functional group are restricted to those functional group(s) and/or atom(s) other than carbon and hydrogen which do not complex with a metal compound and/or are inert under the process conditions defined herein. Thus, the term or variation of the term "organyl group consisting of inert functional groups" further defines the particular organyl groups that can be present within the organyl group consisting of inert functional groups. Additionally, the term "organyl group consisting of inert functional groups" can refer to the presence of one or more inert functional groups within the organyl group. The term or variation of the term "organyl group consisting of inert functional groups" includes the hydrocarbyl group as a member (among other groups). Similarly, an "organylene group consisting of inert functional groups" refers to an organic group formed by removing two hydrogen atoms from one or two carbon atoms of an organic compound consisting of inert functional groups and an "organic group consisting of inert functional groups" refers to a generalized organic group consisting of inert functional groups formed by removing one or more hydrogen atoms from one or more carbon atoms of an organic compound consisting of inert functional groups.

For purposes of this application, an "inert functional group" is a group which does not substantially interfere with the process described herein in which the material having an inert functional group takes part and/or does not complex with the metal compound of the metal complex. The term "does not complex with the metal compound" can include groups that could complex with a metal compound but in particular molecules described herein may not complex with a metal compound due to its positional relationship within a ligand. For example, while an ether group can complex with a metal compound, an ether group located at a para position of a substituted phenyl phosphinyl group in an $N^2$-phosphinyl amidine can be an inert functional group because a single metal compound cannot complex with both the para ether group and the $N^2$-phosphinyl amidine group of the same metal complex molecule. Thus, the inertness of a particular functional group is not only related to the functional group's inherent inability to complex the metal compound but can also be related to the functional group's position within the metal complex. Non-limiting examples of inert functional groups which do not substantially interfere with processes described herein can include halo (fluoro, chloro, bromo, and iodo), nitro, hydrocarboxy groups (e.g., alkoxy, and/or aroxy, among others), sulfidyl groups, and/or hydrocarbyl groups, among others.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group), from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g., halogenated alkane indicates the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl groups are derived by removal of a hydrogen atom from a primary, secondary, or tertiary carbon atom, respectively, of an alkane. The n-alkyl group can be derived by removal of a hydrogen atom from a terminal carbon atom of a linear alkane.

A cycloalkane is a saturated cyclic hydrocarbon, with or without side chains, for example, cyclobutane. Unsaturated cyclic hydrocarbons having one or more endocyclic double or one triple bond are called cycloalkenes and cycloalkynes, respectively. Cycloalkenes and cycloalkynes having only one, only two, only three, etc. endocyclic double or triple bonds, respectively, can be identified by use of the term "mono," "di," "tri," etc. . . . within the name of the cycloalkene or cycloalkyne. Cycloalkenes and cycloalkynes can further identify the position of the endocyclic double or triple bonds.

A "cycloalkyl group" is a univalent group derived by removing a hydrogen atom from a ring carbon atom of a cycloalkane. For example, a 1-methylcyclopropyl group and a 2-methylcyclopropyl group are illustrated as follows.

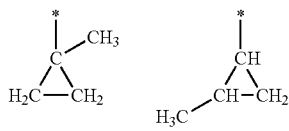

Similarly, a "cycloalkylene group" refers to a group derived by removing two hydrogen atoms from a cycloalkane, at least one of which is a ring carbon. Thus, a "cycloalkylene group" includes both a group derived from a cycloalkane in which two hydrogen atoms are formally removed from the same ring carbon, a group derived from a cycloalkane in which two hydrogen atoms are formally removed from two different ring carbons, and a group derived from a cycloalkane in which a first hydrogen atom is formally removed from a ring carbon and a second hydrogen atom is formally removed from a carbon atom that is not a ring carbon. A "cycloalkane group" refers to a generalized group formed by removing one or more hydrogen atoms (as necessary for the particular group and at least one of which is a ring carbon), from a cycloalkane. It should be noted that according to the definitions provided herein, general cycloalkane groups (including cycloalkyl groups and cycloalkylene groups), include those having zero, one, or more than one hydrocarbyl substituent groups attached to a cycloalkane ring carbon atom (e.g., a methylcyclopropyl group), and are members of the group of hydrocarbon groups. However, when referring to a cycloalkane group having a specified number of cycloalkane ring carbon atoms (e.g., cyclopentane group or cyclohexane group, among others), the base name of the cycloalkane group having a defined number of cycloalkane ring carbon atoms refers to the unsubstituted cycloalkane group (including having no hydrocarbyl groups located on cycloalkane group ring carbon atom). Consequently, a substituted cycloalkane group having a specified number of ring carbon atoms (e.g., substituted cyclopentane or substituted cyclohexane, among others), refers to the respective group having one or more substituent groups (including halogens, hydrocarbyl groups, or hydrocarboxy groups, among other substituent groups) attached to a cycloalkane group ring carbon atom. When the substituted cycloalkane group having a defined number of cycloalkane ring carbon atoms is a member of the group of hydrocarbon groups (or a member of the general group of cycloalkane groups), each substituent of the substituted cycloalkane group having a defined number of cycloalkane ring carbon atoms is limited to a hydrocarbyl substituent group. One can readily discern and select general groups, specific groups, and/or individual substituted cycloalkane group(s) having a specific number of ring carbons atoms which can be utilized as member of the hydrocarbon group (or a member of the general group of cycloalkane groups).

The term "olefin" whenever used in this specification and claims refers to hydrocarbons that have at least one carbon-carbon double bond that is not part of an aromatic ring or ring system. The term "olefin" includes aliphatic and aromatic, acyclic and cyclic, and/or linear and branched compounds having at least one carbon-carbon double bond that is not part of an aromatic ring or ring system unless specifically stated otherwise. Olefins having only one, only two, only three, etc. carbon-carbon double bonds can be identified by use of the term "mono," "di," "tri," etc. . . . within the name of the olefin. The olefins can be further identified by the position of the carbon-carbon double bond(s).

The term "alkene" whenever used in this specification and claims refers a linear or branched hydrocarbon olefin that has one or more carbon-carbon double bonds. Alkenes having only one, only two, only three, etc. such multiple bonds can be identified by use of the term "mono," "di." "tri," etc. . . . within the name. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replaced with a halogen atom.

The term "alpha olefin" as used in this specification and claims refers to an olefin that has a carbon-carbon double bond between the first and second carbon atom of the longest contiguous chain of carbon atoms. The term "alpha olefin" includes linear and branched alpha olefins unless expressly stated otherwise. In the case of branched alpha olefins, a branch can be at the 2 position (a vinylidene) and/or the 3 position or higher with respect to the olefin double bond. The term "vinylidene" whenever used in this specification and claims refers to an alpha olefin having a branch at the 2 position with respect to the olefin double bond. By itself, the term "alpha olefin" does not indicate the presence or absence of other carbon-carbon double bonds unless explicitly indicated. The term "linear alpha olefin" as used herein refers to a non-branched alpha olefin having a carbon-carbon double bond between the first and second carbon atom.

The term "normal alpha olefin" whenever used in this specification and claims refers to a linear hydrocarbon mono-olefin having a carbon-carbon double bond between the first and second carbon atom. It is noted that "normal alpha olefin" is not synonymous with "linear alpha olefin" as the term "linear alpha olefin" can include linear olefinic compounds having a double bond between the first and second carbon atoms and additional double bonds.

An aliphatic compound is an acyclic or cyclic, saturated or unsaturated carbon compound, excluding aromatic compounds. Thus, an aliphatic compound is an acyclic or cyclic, saturated or unsaturated carbon compound, excluding aromatic compounds; that is, an aliphatic compound is a non-aromatic organic compound. An "aliphatic group" is a generalized group formed by removing one or more hydrogen atoms (as necessary for the particular group) from the carbon atom of an aliphatic compound. Aliphatic compounds and therefore aliphatic groups can contain organic functional group(s) and/or atom(s) other than carbon and hydrogen.

An aromatic compound is a compound containing a cyclically conjugated double bond system that follows the Hückel (4n+2) rule and contains (4n+2) pi-electrons, where n is an integer from 1 to 5. Aromatic compounds include "arenes" (hydrocarbon aromatic compounds) and "heteroarenes," also termed "hetarenes" which are heteroaromatic compounds formally derived from arenes by replacement of one or more methine (—C≡) carbon atoms of the cyclically conjugated double bond system with a trivalent or divalent heteroatom, in such a way as to maintain the continuous pi-electron system characteristic of an aromatic system and a number of out-of-plane pi-electrons corresponding to the Hückel rule (4n+2). While arene compounds and heteroarene compounds are mutually exclusive members of the group of aromatic compounds, a compound that has both an arene group and a heteroarene group is generally considered a heteroarene compound. Aromatic compounds, arenes, and heteroarenes can be monocyclic (e.g., benzene, toluene, furan, pyridine, methylpyridine) or polycyclic unless otherwise specified. Polycyclic aromatic compounds, arenes, and heteroarenes, include, unless otherwise specified, compounds wherein the aromatic rings can be fused (e.g., naphthalene, benzofuran, and indole), compounds where the aromatic groups can be separate and joined by a bond (e.g., biphenyl or 4-phenylpyridine), or compounds where the aromatic groups are joined by a group containing linking atoms (e.g., carbon in the methylene group in diphenylmethane; oxygen in diphenyl ether; nitrogen in triphenyl amine, among other linking groups). As disclosed herein, the term "substituted" can be used to describe an aromatic group, arene, or heteroarene wherein a non-hydrogen moiety formally replaces a hydrogen in the compound, and is intended to be non-limiting.

An "aromatic group" refers to a generalized group formed by removing one or more hydrogen atoms (as necessary for the particular group and at least one of which is an aromatic ring carbon atom) from an aromatic compound. For a univalent "aromatic group," the removed hydrogen atom must be from an aromatic ring carbon. For an "aromatic group" formed by removing more than one hydrogen atom from an aromatic compound, at least one hydrogen atom must be from an aromatic hydrocarbon ring carbon. Additionally, an "aromatic group" can have hydrogen atoms removed from the same ring of an aromatic ring or ring system (e.g., phen-1,4-ylene, pyridin-2,3-ylene, naphth-1,2-ylene, and benzofuran-2,3-ylene), hydrogen atoms removed from two different rings of a ring system (e.g., naphth-1,8-ylene and benzofuran-2,7-ylene), or hydrogen atoms removed from two isolated aromatic rings or ring systems (e.g., bis(phen-4-ylene)methane).

An "aralkyl group" is an aryl-substituted alkyl group having a free valance at a non-aromatic carbon atom (e.g., a benzyl group, or a 2-phenyleth-1yl group, among others). Similarly, an "aralkylene group" is an aryl-substituted alkylene group having two free valencies at a single non-aromatic carbon atom or a free valence at two non-aromatic carbon atoms while an "aralkane group" is an aryl-substituted alkane group having one or more free valencies at a non-aromatic carbon atom(s). It should be noted that according the definitions provided herein, general aralkane groups include those having zero, one, or more than one hydrocarbyl substituent groups located on an aralkane aromatic hydrocarbon ring or ring system carbon atom and are members of the group of hydrocarbon groups. However, specific aralkane groups specifying a particular aryl group (e.g., the phenyl group in a benzyl group or a 2-phenylethyl group, among others) refer to the specific unsubstituted aralkane groups (including no hydrocarbyl group located on the aralkane aromatic hydrocarbon ring or ring system carbon atom). Consequently, a substituted aralkane group specifying a particular aryl group refers to a respective aralkane group having one or more substituent groups (including halogens, hydrocarbyl groups, or hydrocarboxy groups, among others). When the substituted aralkane group specifying a particular aryl group is a member of the group of hydrocarbon groups (or a member of the general group of aralkane groups), each substituent is limited to a hydrocarbyl substituent group. One can readily discern and select substituted aralkane groups specifying a particular aryl group which can be utilized as a member of the group of hydrocarbon groups (or a member of the general group of aralkane groups).

A "halide" has its usual meaning; therefore, examples of halides include fluoride, chloride, bromide, and iodide.

A "perfluorohydrocarbyl group" is a hydrocarbyl group wherein two or more carbon-hydrogen bonds are replaced with carbon-fluorine bonds. In some aspects, perfluorohydrocarbyl groups can comprise structures wherein all of the carbon-hydrogen bonds are replaced by carbon-fluorine bonds.

A "perfluoroalkyl group" is an alkyl group wherein two or more carbon-hydrogen bonds are replaced with carbon-fluorine bonds. In some aspects, perfluoroalkyl groups can comprise structures wherein all of the carbon-hydrogen bonds are replaced by carbon-fluorine bonds.

A "perfluoroaryl group" is an aryl group wherein two or more carbon-hydrogen bonds are replaced with carbon-fluorine bonds. In some aspects, perfluoroaryl groups can comprise structures wherein all of the carbon-hydrogen bonds are replaced by carbon-fluorine bonds.

A "perfluorophenyl group" is a phenyl group wherein two or more carbon-hydrogen bonds are replaced with carbon-fluorine bonds. In some aspects, perfluorophenyl groups can comprise structures wherein all of the carbon-hydrogen bonds are replaced by carbon-fluorine bonds.

The terms "room temperature" or "ambient temperature" are used herein to describe any temperature from 15° C. to 35° C. wherein no external heat or cooling source is directly applied. Accordingly, the terms "room temperature" and "ambient temperature" encompass the individual temperatures and any and all ranges, subranges, and combinations of subranges of temperatures from 15° C. to 35° C. wherein no external heating or cooling source is directly applied. The term "atmospheric pressure" is used herein to describe an earth air pressure wherein no external pressure modifying means is utilized. Generally, unless practiced at extreme earth altitudes, "atmospheric pressure" is about 1 atmosphere (alternatively, about 14.7 psi or about 101 kPa). References to gaseous, liquid, and/or solid materials refer to the physical state of the material at 25° C. and atmospheric pressure.

Features within this disclosure that are provided as minimum values can be alternatively stated as "at least" or "greater than or equal to" any recited minimum value for the feature disclosed herein. Features within this disclosure that are provided as maximum values can be alternatively stated as "less than or equal to" for the feature disclosed herein.

Within this disclosure, the normal rules of organic nomenclature will prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. By way of another example, reference to a 3-substituted naphth-2-yl indicates that there is a non-hydrogen substituent located at the 3 position and hydrogens located at the 1, 4, 5, 6, 7, and 8 positions. References to compounds or groups having substitutions at positions in addition to the indicated position will be referenced using "comprising" or some other alternative language. For example, a reference to a phenyl group comprising a substituent at the 4 position refers to a group having a non-hydrogen atom at the 4 position and hydrogen or any non-hydrogen group at the 2, 3, 5, and 6 positions.

Processes for forming oligomer products are described herein. Such processes generally comprise contacting ethylene and a catalyst system (or alternatively, contacting ethylene and the components of the catalyst system) to form an oligomer product under oligomerization conditions.

The term "reaction zone effluent" and its derivatives generally refers to all materials which exit the reaction zone. The materials that can exit the reaction zone include reaction feed(s) (e.g., ethylene, catalyst system or catalyst system components, and/or organic reaction medium), and/or reaction product(s) (e.g., oligomer product including oligomers and non-oligomers). The term "reaction zone effluent" and its derivatives can be qualified to refer to certain portions by use of additional qualifying terms. For example, while reaction zone effluent refers to all materials which exits the reaction zone, a reaction zone oligomer product effluent refers to only the oligomer product within the reaction zone effluent.

The term "oligomerization," and its derivatives, refers to processes which produce a mixture of products containing at least 70 weight percent products containing from 2 to 30 ethylene units. Similarly, as used herein an "oligomer" is a product that contains from 2 to 30 ethylene units while an "oligomerization product" or "oligomer product" includes all products made by the process including the "oligomers" and products which are not "oligomers" (e.g., products which contain more than 30 ethylene units). Further the terms "oligomer product" and "oligomerization product" can be used interchangeably.

The term "trimerization," and its derivatives, refers to a process which produces a mixture of products containing at least 70 weight percent products containing three and only three ethylene units. A "trimer" is a product which contains three and only three ethylene units while a "trimerization product" includes all products made by the trimerization process including trimers and products which are not trimers (e.g., dimers or tetramers). Generally, a "trimerization" process using ethylene produces an oligomer product containing at least 70 weight percent hexene(s).

The term "tetramerization," and its derivatives, refers to a process which produces a mixture of products containing at least 70 weight percent products containing four and only four ethylene units. A "tetramer" is a product which contains four and only four ethylene units while a "tetramerization product" includes all products made by the tetramerization process including tetramers and products which are not tetramers (e.g., dimers or trimers). Generally, a "tetramerization" process using ethylene produces an oligomer product containing at least 70 weight percent octene(s).

The term "trimerization and tetramerization," and its derivatives, refers to a process which produces a mixture of products containing at least 70 weight percent products containing three and/or four and only three and/or four ethylene units. A "trimerization and tetramerization product" includes all products made by the "trimerization and tetramerization" process including trimers, tetramers, and products which are not trimers or tetramers (e.g., dimers). Generally, a "trimerization and tetramerization" process using ethylene produces an oligomer product containing at least 70 weight percent hexene(s) and/or octene(s).

Unless otherwise specified, the terms "contacted," "combined," and "in the presence of" refer to any addition sequence, order, or concentration for contacting or combining two or more components of the oligomerization process. Combining or contacting of oligomerization components, according to the various methods described herein, can occur in one or more contact zones under suitable contact conditions such as temperature, pressure, contact time, flow rates, etc. The contact zone can be disposed in a vessel (e.g., a storage tank, tote, container, mixing vessel, reactor, etc.), a length of pipe (e.g., a tee, inlet, injection port, or header for combining component feed lines into a common line), or any other suitable apparatus for bringing the components into contact. The processes can be carried out in a batch or continuous process as can be suitable for a given embodiment.

Use of the term "optionally" with respect to any element of a claim is intended to mean that the subject element is required, or alternatively, is not required. Both alternatives are intended to be within the scope of the claim.

Processes described herein can utilize steps, features, compounds and/or equipment which are independently described herein. The processes described herein may or may not utilize step identifiers (e.g., 1), 2), etc., a), b), etc., i), ii), etc., or first, second, etc., among others), feature identifiers (e.g., 1), 2), etc., a), b), etc., i), ii), etc., or first, second, etc., among others), and/or compound and/or composition identifiers (e.g., 1), 2), etc., a), b), etc., i), ii), etc., or first, second, etc., among others). However, it should be noted that processes described herein can have multiple steps, features (e.g., reagent ratios, formation conditions, among other considerations), and/or multiple compounds and/or compositions using no descriptor or sometimes having the same general identifier. Consequently, it should be noted that the processes described herein can be modified to use an appropriate step or feature identifier (e.g., 1), 2), etc., a), b), etc., i), ii), etc., or first, second, etc., among others), feature identifier (e.g., 1), 2), etc., a), b), etc., i), ii), etc., or first, second, etc., among others), and/or compound identifier (e.g., first, second, etc.) regardless of step, feature, and/or compound identifier utilized in a particular aspect and/or embodiment described herein and that step or feature identifiers can be added and/or modified to indicate individual different steps/features/compounds utilized within the processes without detracting from the general disclosure.

This disclosure encompasses perfluorohydrocarbyl-$N^2$-phosphinyl amidines (which can also be referred to as ligands), perfluorohydrocarbyl-$N^2$-phosphinyl amidine chromium salt complexes, catalyst systems comprising the perfluorohydrocarbyl-$N^2$-phosphinyl amidine chromium salt complexes (or comprising a chromium salt and the perfluorohydrocarbyl-$N^2$-phosphinyl amidine), and methods of oligomerizing ethylene utilizing perfluorohydrocarbyl-$N^2$-phosphinyl amidine chromium salt complexes (or utilizing a chromium salt and the perfluorohydrocarbyl-$N^2$-phosphinyl amidine), among other aspects and embodiments. While aspects can be disclosed under headings, the headings do not limit the disclosure found therein. Additionally, the various aspects and embodiments disclosed herein can be combined in any manner.

Generally, the perfluorohydrocarbyl-$N^2$-phosphinyl amidines and perfluorohydrocarbyl-$N^2$-phosphinyl amidine chromium salt complexes encompassed by this disclosure have at least one perfluorohydrocarbyl-$N^2$-phosphinyl amidine group. In an embodiment, the perfluorohydrocarbyl-$N^2$-phosphinyl amidine and perfluorohydrocarbyl-$N^2$-phosphinyl amidine chromium salt complexes can comprise only one perfluorohydrocarbyl-$N^2$-phosphinyl amidine group; or alternatively, can comprise only two perfluorohydrocarbyl-$N^2$-phosphinyl amidine groups. In an embodiment, the perfluorohydrocarbyl-$N^2$-phosphinyl amidines, regardless of the number of perfluorohydrocarbyl-$N^2$-phosphinyl amidine groups, or structure, can be non-metallic (i.e., a non-metallic perfluorohydrocarbyl-$N^2$-phosphinyl amidine or a non-metallic compound having a perfluorohydrocarbyl-$N^2$-phosphinyl amidine group). In some embodiments, the amidine group of the perfluorohydrocarbyl-$N^2$-phosphinyl amidine and/or the perfluorohydrocarbyl-$N^2$-phosphinyl amidine chromium salt complexes can be an acyclic amidine group (an amidine group wherein the two nitrogen atoms and the central carbon atom of the amine group are not contained in a ring).

In an embodiment, the perfluorohydrocarbyl-$N^2$-phosphinyl amidine can be a perfluorohydrocarbyl-$N^2$-phosphinyl amidine having Structure PFHNPA I. In an embodiment, the perfluorohydrocarbyl-$N^2$-phosphinyl amidine chromium salt complex can be a perfluorohydrocarbyl-$N^2$-phosphinyl amidine chromium salt complex having Structure PFHNPACr I.

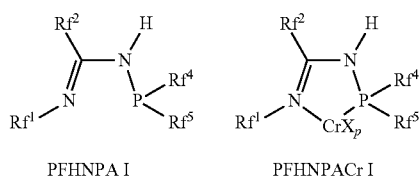

PFHNPA I          PFHNPACr I

Within the perfluorohydrocarbyl-$N^2$-phosphinyl amidine having Structure PFHNPA I, $Rf^1$, $Rf^2$, $Rf^4$, and $Rf^5$ are independent elements of the perfluorohydrocarbyl-$N^2$-phosphinyl amidine having Structure PFHNPA I and are independently described herein. The independent descriptions of $Rf^1$, $Rf^2$, $Rf^4$ and $Rf^5$ can be utilized without limitation, and in any combination, to describe the perfluorohydrocarbyl-$N^2$-phosphinyl amidine having Structure PFHNPA I which can be utilized in any aspect and/or embodiment described herein. Within the perfluorohydrocarbyl-$N^2$-phosphinyl amidine chromium salt complex having Structure PFHN-PACr I, $Rf^1$, $Rf^2$, $Rf^4$, and $Rf^5$ of the perfluorohydrocarbyl-$N^2$-phosphinyl amidine having Structure PFHNPA I and chromium salt, $CrX_p$, are independent elements of the perfluorohydrocarbyl-$N^2$-phosphinyl amidine chromium salt complex having Structure PFHNPACr I and are independently described herein. The independent description of $Rf^1$, $Rf^2$, $Rf^4$, $Rf^5$, and $CrX_p$ can be utilized without limitation, and in any combination, to describe the perfluorohydrocarbyl-$N^2$-phosphinyl amidine chromium salt complex having Structure PFHNPACr I which can be utilized in any aspect and/or embodiment described herein.

Generally, $Rf^1$, $Rf^2$, $Rf^4$, and $Rf^5$ can each independently be a perfluorohydrocarbyl group. In an embodiment, $Rf^1$, $Rf^2$, $Rf^4$, and $Rf^5$ can each independently be a $C_1$ to $C_{20}$ perfluorohydrocarbyl group, a $C_1$ to $C_{15}$ perfluorohydrocarbyl group, or a $C_1$ to $C_{10}$ perfluorohydrocarbyl group. For example, $Rf^1$, $Rf^2$, $Rf^4$, and $Rf^5$ can each independently be a mono-trifluoromethylphenyl group, a di-trifluoromethylphenyl group, or a tri-trifluoromethylphenyl group. Alternatively, $Rf^1$, $Rf^2$, $Rf^4$, and $Rf^5$ can each independently be a mono-trifluoromethylphenyl group; alternatively, a di-trifluoromethylphenyl group; or alternatively, a tri-trifluoromethylphenyl group.

In an aspect, $Rf^1$, $Rf^2$, $Rf^4$ and $Rf^5$ can each independently be a perfluoroalkyl group or a perfluoroaryl group. In an embodiment $Rf^1$, $Rf^2$, $Rf^4$, and $Rf^5$ can each independently be a perfluoroalkyl group. In an alternative embodiment $Rf^1$, $Rf^2$, $Rf^4$, and $Rf^5$ can each independently be a perfluoroaryl group. For example, $Rf^1$, $Rf^2$, $Rf^4$, and $Rf^5$ can each independently be a $C_1$ to $C_{20}$ perfluoroalkyl group, a $C_1$ to $C_{10}$ perfluoroalkyl group, or a $C_1$ to $C_5$ perfluoroalkyl group. In such aspects, $Rf^1$, $Rf^2$, $Rf^4$, and $Rf^5$ can each independently be a trifluoromethyl group, a 1,1-difluoroethyl group, or a pentafluoroethyl group. For example, $Rf^1$, $Rf^2$, $Rf^4$, and $Rf^5$ can each independently be a trifluoromethyl group, alternatively a 1,1-difluoroethyl group, or alternatively a pentafluoroethyl group.

In an aspect, $Rf^1$, $Rf^2$, $Rf^4$, and $Rf^5$ can each independently be a $C_6$ to $C_{20}$ perfluoroaryl group, a $C_6$ to $C_{15}$ perfluoroaryl group, or a $C_6$ to $C_{10}$ perfluoroaryl group. In an aspect $Rf^1$, $Rf^2$, $Rf^4$, and $Rf^5$ can each independently be a $C_6$ to $C_{20}$ perfluorophenyl group. For example and without limitation $Rf^1$, $Rf^2$, $Rf^4$, and $Rf^5$ can each independently be a 2,4-diflurophenyl group, a 2,5-diflurophenyl group, a 3,5, difluorophenyl group, a 2,4,6-trifluorophenyl group, or a 2,3,4,5,6-pentafluorophenyl group. In some embodiments, $Rf^1$, $Rf^2$, $Rf^4$, and $Rf^5$ can each independently be a diflurophenyl group; alternatively, a 2,5-diflurophenyl group; alternatively, a 3,5, difluorophenyl group; alternatively, a 2,4,6-trifluorophenyl group; or alternatively, a 2,3,4,5,6-pentafluorophenyl group.

Various aspects and/or embodiments disclosed herein can utilize a chromium salt or a perfluorohydrocarbyl-$N^2$-phosphinyl amidine chromium salt complex having structure PFHNPACr I. Generally, the chromium salt and/or the chromium salt of the perfluorohydrocarbyl-$N^2$-phosphinyl amidine chromium salt complexes having structure PFHN-PACr I can have the formula $CrX_p$ where X represents a monoanionic ligand and p represents the number of monoanionic ligands (and the oxidation state of the chromium in the chromium compound). The monoanionic ligand (X) and p are independent elements of the chromium salt and the chromium salt portion of the perfluorohydrocarbyl-$N^2$-phosphinyl amidine chromium salt complex having structure PFHNPACr I and are independently described herein. These independent descriptions of the monoanionic ligand (X) and p can be utilized without limitation, and in any combination, to further describe the chromium salt and/or the chromium salt of the perfluorohydrocarbyl-$N^2$-phosphinyl amidine chromium salt complexes having structure PFHNPACr I which can be utilized in various aspects and embodiments described herein.

Generally, the chromium atom of the chromium salt ($CrX_p$), and/or the chromium salt of the perfluorohydrocarbyl-$N^2$-phosphinyl amidine chromium salt complex having structure PFHNPACr I can have any positive oxidation state available to the chromium atom. In an embodiment, the chromium atom of the chromium salt ($CrX_p$) and/or the chromium salt of the perfluorohydrocarbyl-$N^2$-phosphinyl amidine chromium salt complex having structure PFHNPACr I can have an oxidation state of from +2 to +6; alternatively, from +2 to +4; or alternatively, from +2 to +3. In some embodiments, the chromium atom of the chromium salt ($CrX_p$), and/or the chromium salt of the perfluorohydrocarbyl-$N^2$-phosphinyl amidine chromium salt complex having structure PFHNPACr I can have an oxidation state of +2; alternatively, +3; or alternatively, +4.

The monoanion, X, of the chromium salt and/or the chromium salt of the perfluorohydrocarbyl-$N^2$-phosphinyl amidine chromium salt complex having structure PFHNPACr I can be any monoanion. In an embodiment, the monoanion, X, can be a halide, a carboxylate, a β-diketonate, a hydrocarboxide, a nitrate, or a chlorate. In some embodiments, the monoanion, X, can be a halide, a carboxylate, a β-diketonate, or a hydrocarboxide; alternatively, a halide, a carboxylate, or a β-diketonate. In any aspect or embodiment, the hydrocarboxide can be an alkoxide, an aryloxide, or an aralkoxide. Generally, hydrocarboxides (and subdivisions of hydrocarboxides), are the anion analogues of the hydrocarboxy group. In other embodiments, the monoanion, X, can be a halide, a carboxylate, a β-diketonate, or an alkoxide; alternatively, a halide or a carboxylate; or alternatively, a halide or a β-diketonate. In other embodiments, the monoanion X can be a halide; alternatively, a carboxylate; alternatively, a β-diketonate; alternatively, a hydrocarboxide; alternatively, an alkoxide; or alternatively, an aryloxide. Generally, the number, p, of monoanions, X, can equal the oxidation state of the metal atom. In an embodiment, the number, p, of monoanions, X, can be an integer from 2 to 6; alternatively, an integer from 2 to 4; alternatively, an integer from 2 to 3; alternatively, 2; alternatively, 3; or alternatively, 4.

Generally, each halide monoanion, X, of the chromium salt and/or the chromium salt of the perfluorohydrocarbyl-$N^2$-phosphinyl amidine chromium salt complex having structure PFHNPACr I independently can be fluorine, chlorine, bromine, or iodine; or alternatively, chlorine, bromine, or iodine. In an embodiment, each halide monoanion of the chromium salt and/or the chromium salt of the perfluorohydrocarbyl-$N^2$-phosphinyl amidine chromium salt complex having structure PFHNPACr I can be chlorine; alternatively, bromine; or alternatively, iodine. In an embodiment, the monoanion, X, can be chlorine.

Generally, each carboxylate monoanion of the chromium salt and/or the chromium salt of the perfluorohydrocarbyl-$N^2$-phosphinyl amidine chromium salt complex having structure PFHNPACr I independently can be a $C_1$ to $C_{20}$ carboxylate; or alternatively, a $C_1$ to $C_{10}$ carboxylate. In an embodiment, each carboxylate monoanion of the chromium salt and/or the chromium salt of the perfluorohydrocarbyl-$N^2$-phosphinyl amidine chromium salt complex having structure PFHNPACr I independently can be acetate, a propionate, a butyrate, a pentanoate, a hexanoate, a heptanoate, an octanoate, a nonanoate, a decanoate, an undecanoate, a dodecanoate, a tridecanoate, a tetradecanoate, a pentadecanoate, a hexadecanoate, a heptadecanoate, or an octadecanoate; or alternatively, a pentanoate, a hexanoate, a heptanoate, an octanoate, a nonanoate, a decanoate, an undecanoate, or a dodecanoate. In another embodiment, each carboxylate monoanion of the chromium salt and/or the chromium salt of the perfluorohydrocarbyl-$N^2$-phosphinyl amidine chromium salt complex having structure PFHNPACr I independently can be acetate, propionate, n-butyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, laurate (n-dodecanoate), or stearate (n-octadecanoate); alternatively, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, capronate (n-hexanoate); alternatively, n-heptanoate; alternatively, caprylate (n-octanoate); or alternatively, 2-ethylhexanoate. In some embodiments, the carboxylate anion can be triflate (trifluoroacetate).

Generally, each β-diketonate of the chromium salt and/or the chromium salt of the perfluorohydrocarbyl-$N^2$-phosphinyl amidine chromium salt complex having structure PFHNPACr I independently can be any $C_1$ to $C_{20}$ β-diketonate; or alternatively, any $C_1$ to $C_{10}$ β-diketonate. In an embodiment, each β-diketonate of the chromium salt and/or the chromium salt of the perfluorohydrocarbyl-$N^2$-phosphinyl amidine chromium salt complex having structure PFHNPACr I independently can be acetylacetonate (i.e., 2,4-pentanedionate), hexafluoroacetylacetone (i.e., 1,1,1,5,5,5-hexafluoro-2,4-pentanediuonate), or benzoylacetonate; alternatively, acetylacetonate; alternatively, hexafluoroacetylacetone; or alternatively, benzoylacetonate.

Generally, each hydrocarboxide of the chromium salt and/or the chromium salt of the perfluorohydrocarbyl-$N^2$-phosphinyl amidine chromium salt complex having structure PFHNPACr I independently can be any $C_1$ to $C_{20}$ hydrocarboxide; or alternatively, any $C_1$ to $C_{10}$ hydrocarboxide. In an embodiment, each hydrocarboxide of the chromium salt and/or the chromium salt of the perfluorohydrocarbyl-$N^2$-phosphinyl amidine chromium salt complex having structure PFHNPACr I independently can be a $C_1$ to $C_{20}$ alkoxide; alternatively, a $C_1$ to $C_{10}$ alkoxide; alternatively, a $C_6$ to $C_{20}$ aryloxide; or alternatively, a $C_6$ to $C_{10}$ aryloxide. In an embodiment, each alkoxide monoanion independently can be methoxide, ethoxide, propoxide, or butoxide. In an embodiment, each alkoxide monoanion of the chromium salt and/or the chromium salt of the perfluorohydrocarbyl-$N^2$-phosphinyl amidine chromium salt complex having structure PFHNPACr I independently can be methoxide, ethoxide, isopropoxide, or tert-butoxide; alternatively, methoxide; alternatively, ethoxide; alternatively, isopropoxide; or alternatively, tert-butoxide. In an aspect, the aryloxide can be phenoxide.

In a non-limiting embodiment, the chromium salt and/or the chromium salt of any of the perfluorohydrocarbyl-$N^2$-phosphinyl amidine chromium salt complexes having structure PFHNPACr I can comprise, can consist essentially of, or can consist of, a chromium(II) halide, a chromium(III) halide, a chromium(II) carboxylate, chromium(II) carboxylate, a chromium(II) D-diketonate, or a chromium(III) β-diketonate; or alternatively, a chromium(II) halide, a chromium(III) halide, a chromium(II) carboxylate, or a chromium(III) carboxylate. In some non-limiting embodiments, the chromium salt and/or the chromium salt of any of the perfluorohydrocarbyl-$N^2$-phosphinyl amidine chromium salt complex having structure PFHNPACr I can comprise, can consist essentially of, or can consist of, a chromium(II) halide, a chromium(II) carboxylate, or a chromium(II) f-diketonate; or alternatively, a chromium(III) halide, a chromium(III) carboxylate, or a chromium(III) D-diketonate. In other non-limiting embodiments, the chromium salt and/or the chromium salt of any of the perfluorohydrocarbyl-$N^2$-phosphinyl amidine chromium salt complex having structure PFHNPACr I can comprise, can consist essentially of, or can consist of, a chromium(II) halide or a chromium (II) carboxylate; alternatively, a chromium(II) halide or chromium(II) β-diketonate; alternatively, a chromium(III) halide or chromium(III) β-diketonate; alternatively, a chromium(III) halide or a chromium(III) carboxylate; alternatively, a chromium(II) halide; alternatively, a chromium(III) halide; alternatively, a chromium (II) carboxylate; alternatively, a chromium(III) carboxylate; alternatively, a chromium(II) β-diketonate; or alternatively, a chromium(III) β-diketonate.

In a non-limiting embodiment, the chromium salt and/or the chromium salt of any perfluorohydrocarbyl-$N^2$-phosphinyl amidine chromium salt complex having structure PFHNPACr I can comprise, can consist essentially of, or can consist of, chromium(II) chloride, chromium(III) chloride, chromium(II) fluoride, chromium(IIII) fluoride, chromium (II) bromide, chromium(II) bromide, chromium(II) iodide, chromium(III) iodide, chromium(II) acetate, chromium(III) acetate, chromium(II) 2-ethylhexanoate, chromium(III) 2-ethylhexanoate, chromium(II) triflate, chromium(III) triflate, chromium(II) nitrate, chromium(III) nitrate, chromium (II) acetylacetonate, chromium(III) acetylacetonate, chromium(II) hexafluoracetylacetonate, chromium(III) hexafluoracetylacetonate, chromium(III) benzoylacetonate, or chromium(III) benzoylacetonate. In some non-limiting embodiments, the chromium salt and/or the chromium salt of any perfluorohydrocarbyl-$N^2$-phosphinyl amidine chromium salt complex having structure PFHNPACr I can comprise, can consist essentially of, or can consist of, chromium(III) chloride, chromium(III) fluoride, chromium (III) bromide, chromium(III) iodide, chromium(III) chloride (THF) complex, chromium(III) fluoride (THF) complex, chromium(III) bromide (THF) complex, chromium(III) iodide (THF) complex, chromium(III) acetate, chromium (III) 2-ethylhexanoate, chromium(III) triflate, chromium (III) nitrate, chromium(III) acetylacetonate, chromium(III) hexafluoracetylacetonate, or chromium(III) benzoylacetonate. In further embodiments, the chromium salt and/or the chromium salt of any perfluorohydrocarbyl-$N^2$-phosphinyl amidine chromium salt complex having structure PFHNPACr I can comprise, can consist essentially of, or can consist of, chromium(III) chloride, or chromium(III) acetylacetonate; alternatively, chromium(III) chloride; or alternatively, chromium(III) acetylacetonate.

In an embodiment, the perfluorohydrocarbyl-$N^2$-phosphinyl amidine chromium salt complexes which can be utilized in any aspect or embodiment calling for a perfluorohydrocarbyl-$N^2$-phosphinyl amidine chromium salt complex can have structure PFHNPACrCl$_3$.

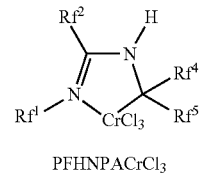

PFHNPACrCl$_3$

Within the perfluorohydrocarbyl-$N^2$-phosphinyl amidine chromium salt complexes having structure PFHNPACrCl$_3$, $Rf^1$, $Rf^2$, $Rf^4$, and $Rf^5$ can be any $Rf^1$, $Rf^2$, $Rf^4$, and $Rf^5$ group described herein. For example, $Rf^1$, $Rf^2$, $Rf^4$, and $Rf^5$ can independently be a $C_1$ to $C_{20}$ perfluorohydrocarbyl group, a $C_1$ to $C_{15}$ perfluorohydrocarbyl group, or a $C_1$ to $C_{10}$ perfluorohydrocarbyl group. In a non-limiting embodiment, $Rf^1$, $Rf^2$, $Rf^4$ and $Rf^5$ can independently be any general or specific perfluoroalkyl group described herein (e.g., a trifluoromethyl group, a 1,1-difluoroethyl group, or a pentafluoroethyl group), any general or specific trifluoromethyl substituted phenyl group disclosed herein (e.g., a mono-trifluoromethylphenyl group, a di-trifluoromethylphenyl group, tri-trifluoromethylphenyl group; or alternatively, a 2-trifluoromethylphenyl group, a 2,6-di-trifluoromethylphenyl group, a 3,5-di-trifluoromethylphenyl group and a 2,4,6-tri-trifluoromethylphenyl group), or any general or specific perfluoroaryl group disclosed herein (e.g., a 2,4-diflurophenyl group, a 2,5-diflurophenyl group, a 3,5, difluorophenyl group, a 2,4,6-trifluorophenyl group, or a 2,3,4,5,6-pentafluorophenyl group).

In some embodiments, the perfluorohydrocarbyl-$N^2$-phosphinyl amidine chromium salt complexes which can be utilized in any aspect or embodiment calling for an perfluorohydrocarbyl-$N^2$-phosphinyl amidine chromium salt complex can have structure CF3NPACrCl$_3$.

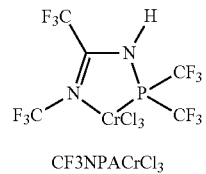

CF3NPACrCl$_3$

It should be noted that while not explicitly shown, the chromium salt and/or the perfluorohydrocarbyl-$N^2$-phosphinyl amidine chromium salt complexes having structure PFHNPACr I or CF3NPACrCl$_3$ can include a neutral ligand. While the chromium salt and the perfluorohydrocarbyl-$N^2$-phosphinyl amidine chromium salt complexes having structure PFHNPACr I or CF3NPACrCl$_3$ do not describe or depict the presence of a neutral ligand, the description and/or the depiction of the chromium salt and/or the perfluorohydrocarbyl-$N^2$-phosphinyl amidine chromium salt complexes having structure PFHNPACr I or CF3NPACrCl$_3$ does not limit the chromium salt and/or the perfluorohydrocarbyl-$N^2$-phosphinyl amidine chromium salt complexes having structure PFHNPACr I or CF3NPACrCl$_3$ to structures not having one or more non-perfluorohydrocarbyl-$N^2$-phosphinyl amidine neutral ligands. In fact, the chromium salt and/or the perfluorohydrocarbyl-$N^2$-phosphinyl amidine chromium salt complexes having structure PFHNPACr I or CF3NPACrCl$_3$ which can be utilized in any embodiment or aspect disclosed herein can include a non-perfluorohydrocarbyl-$N^2$-phosphinyl amidine ligand(s) and the description and/or depictions provided herein do not limit the chromium salt and/or the perfluorohydrocarbyl-$N^2$-phosphinyl amidine chromium salt complexes to those which do not comprise a non-perfluorohydrocarbyl-$N^2$-phosphinyl amidine ligand regardless of the language or structure utilized to describe the chromium salt and/or the perfluorohydrocarbyl-$N^2$-phosphinyl amidine chromium salt complexes having structure PFHNPACr I or CF3NPACrCl$_3$. Non-perfluorohydrocarbyl-$N^2$-phosphinyl amidine neutral ligands are provided herein and can be utilized without limitation and in any combination with the chromium salt and/or the perfluorohydrocarbyl-$N^2$-phosphinyl amidine chromium salt complexes having structure PFHNPACr I or CF3NPACrCl$_3$ to further describe the chromium salt and/or the perfluorohydrocarbyl-$N^2$-phosphinyl amidine chromium salt complexes having structure PFHNPACr I or CF3NPACrCl$_3$ which can be utilized in any embodiment or aspect described herein.

Generally, the non-perfluorohydrocarbyl-$N^2$-phosphinyl amidine neutral ligand, if present, can be any non-perfluorohydrocarbyl-$N^2$-phosphinyl amidine neutral ligand that can form an isolatable compound with the chromium salt and/or the perfluorohydrocarbyl-$N^2$-phosphinyl amidine chromium salt complexes. In an aspect, each non-perfluorohydrocarbyl-$N^2$-phosphinyl amidine neutral ligand independently can be a nitrile, an ether, or an amine; alternatively, a nitrile; alternatively, an ether; or alternatively, an amine. The number of non-perfluorohydrocarbyl-$N^2$-phosphinyl amidine neutral ligands of the chromium salt and the perfluorohydrocarbyl-$N^2$-phosphinyl amidine chromium salt complexes having structure PFHNPACr I or CF3NPACrCl$_3$ can be any number that forms an isolatable compound with the chromium salt and/or the perfluorohydrocarbyl-$N^2$-phosphinyl amidine chromium salt complexes. In an aspect, the number of non-perfluorohydrocarbyl-$N^2$-phosphinyl amidine neutral ligands of the chromium salt and/or the perfluorohydrocarbyl-$N^2$-phosphinyl amidine chromium salt complexes can be 1, 2, 3, 4, 5, or 6; alternatively, 1; alternatively, 2; alternatively, 3; alternatively, 4; alternatively, 5; or alternatively, 6.

Generally, each neutral nitrile ligand which can be utilized as the non-perfluorohydrocarbyl-$N^2$-phosphinyl amidine neutral ligand independently can be a $C_2$ to $C_{20}$ nitrile; or alternatively, a $C_2$ to $C_{10}$ nitrile. In an embodiment, each neutral nitrile ligand independently can be a $C_2$ to $C_{20}$ aliphatic nitrile, a $C_7$ to $C_{20}$ aromatic nitrile, a $C_8$ to $C_{o2}$ aralkane nitrile, or any combination thereof; alternatively, a $C_2$ to $C_{20}$ aliphatic nitrile; alternatively, a $C_7$ to $C_{20}$ aromatic nitrile; or alternatively, a $C_2$ to $C_{20}$ aralkane nitrile. In some embodiments, each neutral nitrile ligand independently can be a $C_2$ to $C_{10}$ aliphatic nitrile, a $C_7$-$C_{10}$ aromatic nitrile, a $C_8$-$C_{10}$ aralkane nitrile, or any combination thereof; alternatively, a $C_1$ to $C_{10}$ aliphatic nitrile; alternatively, a $C_7$ to $C_{10}$ aromatic nitrile; or alternatively, a $C_1$ to $C_{10}$ aralkane nitrile. In an embodiment, each aliphatic nitrile independently can be acetonitrile, propionitrile, butyronitrile, or any combination thereof; alternatively, acetonitrile; alternatively, propionitrile; or alternatively, butyronitrile. In an embodiment, each aromatic nitrile independently can be benzonitrile, 2-methylbenzonitrile, 3-methylbenzonitrile, 4-methylbenzonitrile, 2-ethylbenzonitrile, 3-ethylbenzonitrile, 4-ethylbenzonitrile, or any combination thereof; alternatively, benzonitrile; alternatively, 2-methylbenzonitrile; alternatively, 3-methylbenzonitrile; alternatively, 4-methylbenzonitrile; alternatively, 2-ethylbenzonitrile; alternatively, 3-ethylbenzonitrile; or alternatively, 4-ethylbenzonitrile.

Generally, each neutral ether ligand which can be utilized as the non-perfluorohydrocarbyl-$N^2$-phosphinyl amidine neutral ligand independently can be a $C_2$ to $C_{40}$ ether; alternatively, a $C_2$ to $C_{30}$ ether; or alternatively, a $C_2$ to C) ether. In an embodiment, each neutral ether ligand independently can be a $C_2$ to $C_{40}$ aliphatic ether, a $C_3$ to $C_{40}$ aliphatic cyclic ether, a $C_4$ to $C_{40}$ aromatic cyclic ether; alternatively, a $C_2$ to $C_{40}$ aliphatic acyclic ether or a $C_3$ to $C_{40}$ aliphatic cyclic ether; alternatively, a $C_2$ to $C_{40}$ aliphatic acyclic ether; alternatively, a $C_3$ to $C_{40}$ aliphatic cyclic ether; or alternatively, a $C_4$ to $C_{40}$ aromatic cyclic ether. In some embodiments, each neutral ether ligand independently can be a $C_2$ to $C_{30}$ aliphatic ether, a $C_3$ to $C_{30}$ aliphatic cyclic ether, a $C_4$ to $C_{30}$ aromatic cyclic ether; alternatively, a $C_2$ to $C_3$ aliphatic acyclic ether or a $C_3$ to $C_{30}$ aliphatic cyclic ether; alternatively, a $C_2$ to $C_{30}$ aliphatic acyclic ether; alternatively, a $C_3$ to $C_{30}$ aliphatic cyclic ether; or alternatively, a $C_4$ to $C_{30}$ aromatic cyclic ether. In other embodiments, each neutral ether ligand independently can be a $C_2$ to $C_{20}$ aliphatic ether, a $C_3$ to $C_{20}$ aliphatic cyclic ether, or a $C_4$ to $C_{20}$ aromatic cyclic ether; alternatively, a $C_2$ to $C_{20}$ aliphatic acyclic ether or a $C_1$ to $C_{20}$ aliphatic cyclic ether; alternatively, a $C_2$ to $C_{20}$ aliphatic acyclic ether; alternatively, a $C_3$ to $C_{20}$ aliphatic cyclic ether; or alternatively, a $C_4$ to $C_{20}$ aromatic cyclic ether. In some embodiments, each neutral ether ligand independently can be dimethyl ether, diethyl ether, a dipropyl ether, a dibutyl ether, methyl ethyl ether, a methyl propyl ether, a methyl butyl ether, tetrahydrofuran, a dihydrofuran, 1,3-dioxolane, tetrahydropyran, a dihydropyran, a pyran, a dioxane, furan, benzofuran, isobenzofuran, dibenzofuran, diphenyl ether, a ditolyl ether, or any combination thereof, alternatively, dimethyl ether, diethyl ether, a dipropyl ether, a dibutyl ether, methyl ethyl ether, a methyl propyl ether, a methyl butyl ether, or any combination thereof; alternatively, tetrahydrofuran, a dihydrofuran, 1,3-dioxolane, tetrahydropyran, a dihydropyran, a pyran, a dioxane, or any combination thereof; alternatively, furan, benzofuran, isobenzofuran, dibenzofuran, or any combination thereof; alternatively, diphenyl ether, a ditolyl ether, or any combination thereof; alternatively, dimethyl ether; alternatively, diethyl ether; alternatively, a dipropyl ether; alternatively, a dibutyl ether; alternatively, methyl ethyl ether; alternatively, a methyl propyl ether; alternatively, a methyl butyl ether; alternatively, tetrahydrofuran; alternatively, a dihydrofuran; alternatively, 1,3-dioxolane; alternatively, tetrahydropyran; alternatively, a dihydropyran; alternatively, a pyran; alternatively, a dioxane; alternatively, furan; alternatively, benzofuran; alternatively, isobenzofuran; alternatively, dibenzofuran; alternatively, diphenyl ether; or alternatively, a ditolyl ether.

Throughout this disclosure, the monomeric form of the perfluorohydrocarbyl-$N^2$-phosphinyl amidine chromium salt complex has been depicted. It should be noted that while not explicitly shown, the perfluorohydrocarbyl-$N^2$-phosphinyl amidine chromium salt complexes can exist as dimeric structures having monoanion ligands bridging two chromium atoms. Consequently, while the monomeric perfluorohydrocarbyl-$N^2$-phosphinyl amidine chromium salt complexes are depicted herein, these structures do not necessarily imply that a dimeric form of perfluorohydrocarbyl-$N^2$-phosphinyl amidine chromium salt complexes having bridging monomeric ligands are not formed and/or utilized.

In an aspect, the present disclosure relates to catalyst systems comprising a perfluorohydrocarbyl-$N^2$-phosphinyl amidine chromium salt complex having structure PFHNPACr I; or alternatively, a perfluorohydrocarbyl-$N^2$-phosphinyl amidine having structure PFHNPA I and a chromium salt. In an embodiment, the catalyst system can comprise, or consist essentially of, a perfluorohydrocarbyl-$N^2$-phosphinyl amidine chromium salt complex having structure PFH-NPACr I and an organoaluminum compound; or alternatively, a perfluorohydrocarbyl-N²-phosphinyl amidine chromium salt complex having structure PFHNPACr I and an aluminoxane. In another aspect, the catalyst system can comprise, or consist essentially of, a perfluorohydrocarbyl-N²-phosphinyl amidine having structure PFHNPA I, a chromium salt, and an organoaluminum compound; or alternatively, a perfluorohydrocarbyl-N²-phosphinyl amidine having structure PFHNPA I, a chromium salt, and an aluminoxane. The perfluorohydrocarbyl-N²-phosphinyl amidine having structure PFHNPA I, the chromium salt, the perfluorohydrocarbyl-N²-phosphinyl amidine chromium salt complex having structure PFHNPACr I, the organoaluminum compound, and the aluminoxane which can be utilized in various aspects and/or embodiments of their respective catalyst systems are independently described herein and can be utilized in any combination and without limitation to describe the respective various catalyst systems of this disclosure.

In an aspect, the organoaluminum compound which can be utilized in the processes described herein can comprise an aluminoxane, an alkylaluminum compound, or any combination thereof; alternatively, an aluminoxane; or alternatively, an alkylaluminum compound. In an aspect, the alkylaluminum compound can be a trialkylaluminum, an alkylaluminum halide, an alkylaluminum alkoxide, or any combination thereof. In some aspects, the alkylaluminum compound can be a trialkylaluminum, an alkylaluminum halide, or any combination thereof; alternatively, a trialkylaluminum, an alkylaluminum alkoxide, or any combination thereof; or alternatively, a trialkylaluminum. In other aspects, the alkylaluminum compound can be a trialkylaluminum; alternatively, an alkylaluminum halide, or alternatively, an alkylaluminum alkoxide.

In a non-limiting embodiment, the aluminoxane can have a repeating unit characterized by Formula I:

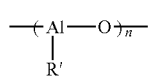

Formula I wherein R' is a linear or branched alkyl group. Alkyl groups for organoaluminum compounds are independently described herein and can be utilized without limitation to further describe the aluminoxanes having Formula I. Generally, n of Formula I can be greater than 1; or alternatively, greater than 2. In an embodiment, n can range from 2 to 15; or alternatively, from 3 to 10.

In an aspect, each halide of any alkylaluminum halide disclosed herein can independently be fluoride, chloride, bromide, or iodide; or alternatively, chloride, bromide, or iodide. In an embodiment, each halide of any alkylaluminum halide disclosed herein can be fluoride; alternatively, chloride; alternatively, bromide; or alternatively, iodide.

In an aspect, each alkyl group of any organoaluminum compound disclosed herein (alkylaluminum trialkylaluminum, alkylaluminum halide, alkylaluminum alkoxide or aluminoxane, among others) independently can be a $C_1$ to $C_{20}$ alkyl group, a $C_1$ to $C_{10}$ alkyl group, or a $C_1$ to $C_6$ alkyl group. In an embodiment, each alkyl group of any organoaluminum compound disclosed herein independently can be a methyl group, an ethyl group, a propyl group, a butyl group, a pentyl group, a hexyl group, a heptyl group, or an octyl group; alternatively, a methyl group, an ethyl group, a butyl group, a hexyl group, or an octyl group. In some embodiments, each alkyl group of any organoaluminum compound disclosed herein independently can be a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group.

In an aspect, each alkoxide group of any alkylaluminum alkoxide disclosed herein independently can be a $C_1$ to $C_{20}$ alkoxy group, a $C_1$ to $C_{10}$ alkoxy group, or a $C_1$ to $C_6$ alkoxy group. In an embodiment, each alkoxide group of any alkylaluminum alkoxide disclosed herein independently can be a methoxy group, an ethoxy group, a propoxy group, a butoxy group, a pentoxy group, a hexoxy group, a heptoxy group, or an octoxy group; alternatively, a methoxy group, an ethoxy group, a butoxy group, a hexoxy group, or an octoxy group. In some embodiments, each alkoxide group of any alkylaluminum alkoxide disclosed herein independently can be a methoxy group, an ethoxy group, an n-propoxy group, an n-butoxy group, an iso-butoxy group, an n-hexoxy group, or an n-octoxy group; alternatively, a methoxy group, an ethoxy group, an n-butoxy group, or an iso-butoxy group; alternatively, a methoxy group; alternatively, an ethoxy group; alternatively, an n-propoxy group; alternatively, an n-butoxy group; alternatively, an iso-butoxy group; alternatively, an n-hexoxy group; or alternatively, an n-octoxy group.

In a non-limiting embodiment, useful trialkylaluminum compounds can include trimethylaluminum, triethylaluminum, tripropylaluminum, tributylaluminum, trihexylaluminum, trioctylaluminum, or mixtures thereof. In some non-limiting embodiments, useful trialkylaluminum compounds can include trimethylaluminum, triethylaluminum, tripropylaluminum, tri-n-butylaluminum, tri-isobutylaluminum, trihexylaluminum, tri-n-octylaluminum, or mixtures thereof; alternatively, triethylaluminum, tri-n-butylaluminum, tri-isobutylaluminum, trihexylaluminum, tri-n-octylaluminum, or mixtures thereof, alternatively, triethylaluminum, tri-n-butylaluminum, trihexylaluminum, tri-n-octylaluminum, or mixtures thereof. In other non-limiting embodiments, useful trialkylaluminum compounds can include trimethylaluminum; alternatively, triethylaluminum; alternatively, tripropylaluminum; alternatively, tri-n-butylaluminum; alternatively, tri-isobutylaluminum; alternatively, trihexylaluminum; or alternatively, tri-n-octylaluminum.

In a non-limiting embodiment, useful alkylaluminum halides can include diethylaluminum chloride, diethylaluminum bromide, ethylaluminum dichloride, ethylaluminum sesquichloride, and mixtures thereof. In some non-limiting embodiments, useful alkylaluminum halides can include diethylaluminum chloride, ethylaluminum dichloride, ethylaluminum sesquichloride, and mixtures thereof. In other non-limiting embodiments, useful alkylaluminum halides can include diethylaluminum chloride; alternatively, diethylaluminum bromide; alternatively, ethylaluminum dichloride; or alternatively, ethylaluminum sesquichloride.

In a non-limiting embodiment, useful aluminoxanes can include methylaluminoxane (MAO), ethylaluminoxane, a modified methylaluminoxane (e.g., a MMAO), n-propylaluminoxane, isopropylaluminoxane, n-butylaluminoxane, sec-butylaluminoxane, iso-butylaluminoxane, t-butylaluminoxane, 1-pentylaluminoxane, 2-pentylaluminoxane, 3-pentylaluminoxane, isopentylaluminoxane, neopentylaluminoxane, or mixtures thereof. In some non-limiting embodiments, useful aluminoxanes can include methylaluminoxane (MAO), a modified methylaluminoxane (e.g., a MMAO), isobutyl aluminoxane, t-butylaluminoxane, or mixtures thereof. In other non-limiting embodiments, useful aluminoxanes can include methylaluminoxane (MAO); alternatively, ethylaluminoxane; alternatively, a modified methylaluminoxane (e.g., a MMAO); alternatively, n-propylaluminoxane; alternatively, isopropylaluminoxane; alternatively, n-butylaluminoxane alternatively, sec-butylaluminoxane; alternatively, iso-butylaluminoxane; alternatively, t-butylaluminoxane; alternatively, 1-pentylaluminoxane; alternatively, 2-pentylaluminoxane; alternatively, 3-pentylaluminoxane; alternatively, isopentylaluminoxane; or alternatively, neopentylaluminoxane.

In an aspect, the organoaluminum compound and the perfluorohydrocarbyl-$N^2$-phosphinyl amidine chromium salt complex having structure PFHNPACr I (or alternatively, the chromium salt) can be combined in any ratio that can form an active catalyst system. In an embodiment, the catalyst system can have a minimum aluminum of the organoaluminum compound to chromium of the perfluorohydrocarbyl-$N^2$-phosphinyl amidine chromium salt complex having structure PFHNPACr I (or alternatively, chromium of the chromium salt) molar ratio (i.e., minimum Al to Cr molar ratio) of 10:1, 50:1, 75:1, or 100:1; alternatively or additionally, and a maximum aluminum of the organoaluminum compound to chromium of the perfluorohydrocarbyl-$N^2$-phosphinyl amidine chromium salt complex having structure PFHNPACr I (or alternatively, chromium of the chromium salt) molar ratio (i.e., maximum Al to Cr molar ratio) of 5,000:1, 3,000:1, 2.000:1, 1,500:1, or 1,000:1. In an embodiment, the catalyst system can have an Al to Cr molar ratio ranging from any minimum Al to Cr molar ratio disclosed herein to any maximum Al to Cr molar ratio disclosed herein. In a non-limiting embodiment, the Al to Cr molar ratio can range from 10:1 to 5.000:1, from 50:1 to 3,000:1, from 75:1 to 2,000:1, from 100:1 to 2,000:1, or from 100:1 to 1,000:1. Other Al to Cr molar ratio ranges that can be utilized are readily apparent to those skilled in the art with the aid of this disclosure.

When the catalyst system utilizes a perfluorohydrocarbyl-$N^2$-phosphinyl amidine having structure PFHNPA 1, a chromium salt, and an organoaluminum compound, the catalyst system can have (or the catalyst system can be formed at), the oligomer product can be formed at, the reaction zone can have, or the reaction zone can operate at any perfluorohydrocarbyl-$N^2$-phosphinyl amidine having structure PFHNPA I to chromium of the chromium salt molar ratio which can form an oligomer product. In an embodiment, the minimum perfluorohydrocarbyl-$N^2$-phosphinyl amidine having structure PFHNPA I to chromium of the chromium salt molar ratio can be 0.8:1, 0.9:1, or 0.95:1; alternatively or additionally, the maximum perfluorohydrocarbyl-$N^2$-phosphinyl amidine having structure PFHNPA I to chromium of the chromium salt molar ratio can be 4:1, 2:1, 1.5:1, or 1.1:1. In an embodiment, the catalyst system can have (or the catalyst system can be formed at), the oligomer product can be formed at, the reaction zone can have, or the reaction zone can operate at a perfluorohydrocarbyl-$N^2$-phosphinyl amidine having structure PFHNPA I to chromium of the chromium salt molar ratio in the range of any minimum perfluorohydrocarbyl-$N^2$-phosphinyl amidine having structure PFHNPA I to chromium of the chromium salt molar ratio disclosed herein to any maximum perfluorohydrocarbyl-$N^2$-phosphinyl amidine having structure PFHNPA I to chromium of the chromium salt molar ratio disclosed herein. In a non-limiting embodiment, the perfluorohydrocarbyl-$N^2$-phosphinyl amidine having structure PFHNPA I to chromium of the chromium salt molar ratio can be in the range of 0.8:1 to 4:1, from 0.9:1 to 2:1, from 0.9:1 to 1.5:1, from 0.95:1 to 1.5:1, or from 0.95:1 to 1.1:1. Other perfluorohydrocarbyl-$N^2$-phosphinyl amidine having structure PFHNPA I to chromium of the chromium salt molar ratio ranges that can be utilized are readily apparent to those skilled in the art with the aid of this disclosure.

In an aspect, the present disclosure relates to an ethylene oligomerization process; alternatively, an ethylene trimerization process; alternatively, an ethylene tetramerization process; or alternatively, an ethylene trimerization and tetramerization process.

In an embodiment, the processes described herein can comprise: a) contacting ethylene and a catalyst system; and b) forming an oligomer product. In some embodiments, the processes described herein can comprise: a) contacting ethylene, hydrogen, and a catalyst system; and b) forming an oligomer product. In some embodiments, the oligomer product can be formed under conditions capable of forming an oligomer product. In some embodiments, the oligomer product can be formed in a reaction zone. In an embodiment, the catalyst system can be formed in an organic liquid medium. In an embodiment, the oligomer product can be formed in (or the reaction zone can include) an organic reaction medium. Generally, the organic liquid medium in which the catalyst system can be formed and the organic reaction medium in which the olefin and the catalyst system can be contacted (or alternatively, in which the oligomer product can be formed) can be the same; or alternatively, can be different. The catalyst system, the conditions under which the oligomer product can be formed (or alternatively, the conditions under which the reaction zone can operate), the organic liquid medium, the organic reaction medium, and features of the oligomer product are independently described herein and can be utilized in any combination, and without limitation, to further describe the processes described herein.

In an embodiment, the processes described herein can comprise: a) forming a catalyst system mixture comprising a perfluorohydrocarbyl-$N^2$-phosphinyl amidine chromium salt complex having structure PFHNPACr I and an organoaluminum compound (or alternatively, forming a catalyst system comprising a perfluorohydrocarbyl-$N^2$-phosphinyl amidine having structure PFHNPA I, a chromium salt, and an organoaluminum compound); b) contacting the catalyst system mixture with ethylene; and c) forming an oligomer product. In some embodiments, the step of contacting the catalyst system mixture with ethylene can be a step of contacting the catalyst system mixture with ethylene and hydrogen. In some embodiments, the catalyst system mixture can further comprise an organic liquid medium. In some embodiments, the catalyst system mixture and ethylene, and optionally hydrogen, can be contacted in or with an organic reaction medium. In an embodiment, the process can comprise: a) forming a catalyst system mixture comprising, or consisting essentially of, the perfluorohydrocarbyl-$N^2$-phosphinyl amidine chromium salt complex having structure PFHNPACr I, an organoaluminum compound, and an organic liquid medium (or alternatively, comprising the perfluorohydrocarbyl-$N^2$-phosphinyl amidine having structure PFHNPA I, a chromium salt, an organoaluminum compound, and an organic liquid medium); b) contacting the catalyst system mixture with ethylene and an organic reaction medium; and c) forming an oligomer product. In some embodiments, the step of contacting the catalyst system mixture with ethylene and the organic liquid medium can be a step of contacting the catalyst system mixture with ethylene, an organic reaction medium, and hydrogen. In some embodiments, the organic liquid medium and the organic reaction medium can be the same; or alternatively, the organic liquid medium and the organic reaction medium can be different. In some embodiments, the oligomer product can be formed in a reaction zone. In some embodiments, the oligomer product can be formed under conditions capable of forming an oligomer product. The perfluorohydrocarbyl-$N^2$-phosphinyl amidine having structure PFHNPA I, the chromium salt, the perfluorohydrocarbyl-$N^2$-phosphinyl amidine chromium salt complex having structure PFHNPACr I, the organoaluminum compound, the organic liquid medium, the organic reaction medium, the conditions under which the oligomer product can be formed (or alternatively, the conditions under which the reaction zone can operate), and features of the oligomer product (among other independently described catalyst system and process features) are independently described herein and can be utilized, without limitation, and in any combination, to further describe the respective processes disclosed herein.

In an embodiment, the processes described herein can comprise: a) forming a composition comprising a perfluorohydrocarbyl-$N^2$-phosphinyl amidine chromium salt complex having structure PFHNPACr I (or alternatively, comprising a perfluorohydrocarbyl-$N^2$-phosphinyl amidine having structure PFHNPA I and a chromium salt); b) forming a mixture comprising ethylene and an organoaluminum compound; c) contacting the composition of step a) and the mixture of step b); and d) forming an oligomer product. In some embodiments, the mixture comprising ethylene and the organoaluminum compound can further comprise hydrogen. In some embodiments, the composition comprising the perfluorohydrocarbyl-$N^2$-phosphinyl amidine chromium salt complex having structure PFHNPACr I can further comprise an organic liquid medium. In some embodiments, the mixture comprising ethylene, an organoaluminum compound, and optionally hydrogen, can further comprise an organic reaction medium. In an embodiment, the process can comprise: a) forming a composition comprising, or consisting essentially of, the perfluorohydrocarbyl-$N^2$-phosphinyl amidine metal complex having structure PFHNPACr I and an organic liquid medium (or alternatively, comprising the perfluorohydrocarbyl-$N^2$-phosphinyl amidine having structure PFHNPACr I, a chromium salt, and an organic liquid medium); b) forming a mixture comprising ethylene, an organoaluminum compound, optionally hydrogen, and an organic reaction medium; c) contacting the composition of step a) and the mixture of step b); and d) forming an oligomer product. In some embodiments, the organic liquid medium and the organic reaction medium can be the same; or alternatively, the organic liquid medium and the organic reaction medium can be different. In some embodiments, the oligomer product can be formed in a reaction zone. In some embodiments, the oligomer product can be formed under conditions capable of forming an oligomer product. The perfluorohydrocarbyl-$N^2$-phosphinyl amidine having structure PFHNPA I, the chromium salt, the perfluorohydrocarbyl-$N^2$-phosphinyl amidine chromium salt complex having structure PFHNPACr I, the organoaluminum compound, the organic liquid medium, the organic reaction medium, the conditions under which the oligomer product can formed (or alternatively, the conditions under which the reaction zone can operate), and features of the oligomer product (among other composition, mixture, oligomer product and process features) are independently described herein and can be utilized, without limitation, and in any combination, to further describe the processes described herein.

In an embodiment, the processes described herein can comprise: a) contacting ethylene and a catalyst system comprising a perfluorohydrocarbyl-$N^2$-phosphinyl amidine chromium salt complex having Structure PFHNPACr I (or alternatively, contacting a perfluorohydrocarbyl-$N^2$-phosphinyl amidine having Structure PFHNPA I and a chromium salt); and b) forming an oligomer product in a reaction zone. In some embodiments, the processes described herein can comprise, a) contacting ethylene, hydrogen, and a catalyst system comprising the $N^2$-phosphinylamidine chromium salt complex having Structure PFHNPACr I (or alternatively, contacting the perfluorohydrocarbyl-$N^2$-phosphinyl amidine having Structure PFHNPA I and a chromium salt); and b) forming an oligomer product in a reaction zone. In other embodiments, the processes described herein can comprise: a) contacting ethylene and a catalyst system comprising the perfluorohydrocarbyl-$N^2$-phosphinyl amidine chromium salt complex having Structure PFHNPACr I and an organoaluminum compound (or alternatively, the perfluorohydrocarbyl-$N^2$-phosphinyl amidine having Structure PFHNPA I and a chromium salt and an organoaluminum compound); and b) forming an oligomer product in a reaction zone. In yet other embodiments, the processes described herein can comprise, a) contacting ethylene, hydrogen, and a catalyst system comprising the perfluorohydrocarbyl-$N^2$-phosphinyl amidine chromium salt complex having Structure PFHNPACr I and an organoaluminum compound (or alternatively, contacting the perfluorohydrocarbyl-$N^2$-phosphinyl amidine having Structure PFHNPA I, a chromium salt, and an organoaluminum compound); and b) forming an oligomer product in a reaction zone. In an embodiment, the respective processes can further comprise forming a catalyst system mixture comprising the catalyst system components. In some embodiments, the catalyst system mixture can be (or can be formed in) an organic liquid medium. In other embodiments of the respective processes, the oligomer product can be formed in (or the reaction zone can include) an organic reaction medium. In some embodiments, the organic liquid medium and the organic reaction medium can be the same; or alternatively, the organic liquid medium and the organic reaction medium can be different. The perfluorohydrocarbyl-$N^2$-phosphinyl amidine having structure PFHNPA I, the chromium salt, the perfluorohydrocarbyl-$N^2$-phosphinyl amidine chromium salt complex having structure PFHNPACr I, the organoaluminum compound, the organic liquid medium, the organic reaction medium, the conditions under which the oligomer product can be formed (or alternatively, the conditions under which the reaction zone can operate), and features of the oligomer product (among other composition, mixture, oligomer product, and process features) are independently described herein and can be utilized, without limitation, and in any combination, to further describe the processes described herein.

In an embodiment, the processes described herein can be a batch process or a continuous process. In some embodiments, the reaction zone of any process described herein can comprise any reactor which can oligomerize, trimerize, tetramerize, or trimerize and tetramerize ethylene to an oligomer product. In some embodiments, the reaction zone can comprise one or more reactors. In some embodiments, the reaction zone can comprise a stirred tank reactor, a plug flow reactor, or any combination thereof; alternatively, a stirred tank reactor; or alternatively, a plug flow reactor. In an embodiment, the reaction zone of any process described herein can comprise an autoclave reactor, a continuous stirred tank reactor, a loop reactor, a gas phase reactor, a solution reactor, a tubular reactor, a recycle reactor, a bubble reactor, or any combination thereof; alternatively, an autoclave reactor; alternatively, a stirred tank reactor; alternatively, a loop reactor; alternatively, a gas phase reactor; alternatively, a solution reactor; alternatively, a tubular reactor; alternatively, a recycle reactor; or alternatively, a bubble reactor. In some embodiments, the reaction zone can comprise multiple reactors, or alternatively, only one reactor. When multiple reactors are present, each of the reactors can be the same; or alternatively, two or more of the reactors can be different. The reaction zone can comprise single or multiple reactors of any type disclosed herein operating in batch or continuous mode and/or in series or parallel.

The processes described herein can use an organic liquid medium and/or an organic reaction medium. Generally, the organic liquid medium and/or the organic reaction medium can act as a solvent and/or a diluent in the processes described herein. In an aspect, the organic liquid medium and/or the organic reaction medium can be a hydrocarbon, a halogenated hydrocarbon, or a combination thereof. Hydrocarbons and halogenated hydrocarbons which can be used as the organic liquid medium and/or the organic reaction medium can include, for example, aliphatic hydrocarbons, aromatic hydrocarbons, petroleum distillates, halogenated aliphatic hydrocarbons, halogenated aromatic hydrocarbons, or combinations thereof. Aliphatic hydrocarbons which can be used as the organic liquid medium and/or the organic reaction medium include $C_3$ to $C_{20}$ aliphatic hydrocarbons. $C_4$ to $C_{15}$ aliphatic hydrocarbons, or $C_5$ to $C_{10}$ aliphatic hydrocarbons. The aliphatic hydrocarbons which can be used as the organic liquid medium and/or the organic reaction medium can be cyclic or acyclic and/or can be linear or branched, unless otherwise specified. Non-limiting examples of suitable acyclic aliphatic hydrocarbon organic liquid mediums and/or organic reaction mediums that can be utilized include propane, isobutane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or a mixture of linear and branched $C_6$ acyclic aliphatic hydrocarbons), heptane (n-heptane or a mixture of linear and branched $C_7$ acyclic aliphatic hydrocarbons), octane (n-octane or a mixture of linear and branched $C_8$ acyclic aliphatic hydrocarbons), or combinations thereof. Non-limiting examples of suitable cyclic aliphatic hydrocarbons which can be used as the organic liquid medium and/or the organic reaction medium include cyclohexane, and methylcyclohexane. Aromatic hydrocarbons which can be used as the organic liquid medium and/or the organic reaction medium include $C_6$ to $C_{10}$ aromatic hydrocarbons. Non-limiting examples of suitable aromatic hydrocarbons that can be utilized as the organic liquid medium and/or the organic reaction medium include benzene, toluene, xylene (including ortho-xylene, meta-xylene, para-xylene, or mixtures thereof), ethylbenzene, or combinations thereof. Halogenated aliphatic hydrocarbons which can be used as the organic liquid medium and/or the organic reaction medium include $C_1$ to $C_{15}$ halogenated aliphatic hydrocarbons, $C_1$ to $C_{10}$ halogenated aliphatic hydrocarbons, or $C_1$ to $C_5$ halogenated aliphatic hydrocarbons. The halogenated aliphatic hydrocarbons which can be used as the organic liquid medium and/or the organic reaction medium can be cyclic or acyclic and/or can be linear or branched, unless otherwise specified. Non-limiting examples of suitable halogenated aliphatic hydrocarbons which can be utilized as the organic liquid medium and/or the organic reaction medium include methylene chloride, chloroform, carbon tetrachloride, dichloroethane, trichloroethane, and any combination thereof. Halogenated aromatic hydrocarbons which can be used as the organic liquid medium and/or the organic reaction medium include $C_6$ to $C_{20}$ halogenated aromatic hydrocarbons or $C_6$ to $C_{10}$ halogenated aromatic hydrocarbons, for example. Non-limiting examples of suitable halogenated aromatic hydrocarbons which can be used as the organic liquid medium and/or the organic reaction medium include chlorobenzene, dichlorobenzene, or combinations thereof.

The choice of organic liquid medium and/or organic reaction medium can be made on the basis of convenience in processing. For example, isobutane can be chosen to be compatible with the organic liquid medium and/or organic reaction medium used in processes using the product(s) of the process described herein (e.g., using the product for the formation of polymer in a subsequent processing step). In some embodiments, the organic liquid medium and/or the organic reaction medium can be chosen to be easily separable from one or more of the oligomers in the oligomer product. In some embodiments, an oligomer of the oligomer product can be utilized as the organic liquid medium and/or the organic reaction medium. For example, when 1-hexene is an oligomer of an ethylene trimerization process or an ethylene trimerization and tetramerization process, 1-hexene can be chosen as the organic liquid medium and/or the organic reaction medium to decrease the need for separation. When 1-octene is an oligomer of an ethylene tetramerization process or ethylene trimerization and tetramerization process, 1-octene can be chosen as the organic liquid medium and/or the organic reaction medium to decrease the need for separation.

Generally, the oligomer product that can be produced using the processes described herein can be formed at conditions (or alternatively, the reaction zone can have any conditions), which can 1) facilitate oligomer product formation, 2) provide a desired oligomer product formation rate, 3) provide acceptable catalyst system productivity, 4) provide acceptable oligomer selectivity, and/or 5) provide acceptable polymer formation. In an embodiment, conditions under which the oligomer product can be formed (or alternatively, the reaction zone can have conditions that), can include one or more of catalyst system component ratios, chromium concentration, pressure, ethylene partial pressure, ethylene concentration, presence of hydrogen (and its partial pressure and/or hydrogen to ethylene mass ratio), temperature, reaction time, single pass ethylene conversion, and/or catalyst system productivity. Catalyst system component ratios, chromium concentration, pressure, ethylene partial pressure, ethylene concentration, presence of hydrogen (and its partial pressure and/or hydrogen to ethylene mass ratio), temperature, reaction time, single pass ethylene conversion, and catalyst system productivity are independently described herein and these independent descriptions can be used without limitation, and in any combination, to describe condition(s) at which the oligomer product can be formed and/or condition(s) at which the reaction zone can operate for any of the processes described herein.

In an embodiment, the oligomer product can be formed (or the reaction zone can operate) at a minimum aluminum of the organoaluminum to chromium of the perfluorohydrocarbyl-$N^2$-phosphinyl amidine chromium salt complex having structure PFHNPACr I (or alternatively, the chromium salt) molar ratio (Al to Cr molar ratio) of 10:1, 50:1, 75:1, or 100:1; alternatively or additionally, at a maximum Al to Cr molar ratio of 5,000:1, 3,000:1, 2,000:1, 1,500:1, or 1,000:1. In an embodiment, the oligomer product can be formed (or the reaction zone can operate) at an Al to Cr molar ratio ranging from any minimum Al to Cr molar ratio disclosed herein to any maximum Al to Cr molar ratio disclosed herein. In a non-limiting embodiment, the Al to Cr molar ratio can range from 10:1 to 5.000:1, from 50:1 to 3,000:1, from 75:1 to 2,000:1, from 100:1 to 2,000:1, or from 100:1 to 1,000:1. Other Al to Cr molar ratio ranges that can be utilized are readily apparent to those skilled in the art with the aid of this disclosure.

In an embodiment, the oligomer product can be formed (or the reaction zone can operate) at a minimum reaction zone chromium of the chromium perfluorohydrocarbyl-$N^2$-phosphinyl amidine chromium salt complex having structure PFHNPACr I (or alternatively, the chromium of the chromium salt) concentration (i.e., minimum chromium concentration) of $1\times10^{-6}$ Cr equivalents/liter, $1\times10^{-5}$ Cr equivalents/liter, or $5\times10^{-4}$ Cr equivalents/liter; alternatively or additionally, at a maximum reaction zone chromium of the perfluorohydrocarbyl-$N^2$-phosphinyl amidine chromium salt complex having structure PFHNPACr I (or alternatively, chromium of the chromium salt) concentration (i.e., maximum chromium concentration) of 1 Cr equivalents/liter, 0.5 Cr equivalents/liter, or 0.1 Cr equivalents/liter. In an embodiment, the oligomer product can be formed (or the reaction zone can operate) at a reaction zone chromium concentration ranging from any minimum chromium concentration disclosed herein to any maximum chromium concentration disclosed herein. In a non-limiting embodiment, the reaction zone chromium concentration can range from $1\times10^{-6}$ Cr equivalents/liter to 1 Cr equivalents/liter, from $1\times10^{-5}$ Cr equivalents/liter to 0.5 Cr equivalents/liter, or from $5\times10^{-4}$ Cr equivalents/liter to 0.1 Cr equivalents/liter. Other chromium concentration ranges that can be utilized are readily apparent to those skilled in the art with the aid of this disclosure.

In an embodiment, the oligomer product can be formed (or the reaction zone can operate) at a minimum pressure of 5 psi (34.5 kPa), 50 psi (345 kPa), 100 psi (689 kPa), 150 psi (1.03 MPa), 250 psi (1.72 MPa), 500 psi (3.5 MPa), or 600 psi (4.1 MPa); alternatively or additionally, at a maximum pressure of 2,500 psi (17.2 MPa), 2,000 psi (13.8 MPa), 1,500 psi (10.3 MPa), 1250 psi (8.62 MPa), or 1000 psi (6.89 MPa). In an embodiment, the oligomer product can be formed (or the reaction zone can operate) at a pressure ranging from any minimum pressure disclosed herein to any maximum pressure disclosed herein. In some non-limiting embodiments, the oligomer product can be formed (or the reaction zone can operate) at a pressure from 5 psi (34.5 kPa) to 2,500 psi (17.2 MPa), from 5 psi (34.5 kPa) to 2,000 psi (13.8 MPa), from 50 psi (345 kPa) to 2,000 psi (13.8 MPa), from 100 psi (689 kPa) to 2,000 psi (13.8 MPa), from 100 psi (689 kPa) to 1,500 psi (10.3 MPa), from 150 psi (1.03 MPa) to 1500 psi (10.3 MPa), from 250 psi (1.72 MPa) to 1250 psi (8.62 MPa), from 500 psi (3.5 MPa) to 1250 psi (8.62 MPa), or from 600 psi (4.1 MPa) to 1000 psi (6.89 MPa). Other pressure ranges that can be utilized are readily apparent to those skilled in the art with the aid of this disclosure.

In an embodiment, the oligomer product can be formed (or the reaction zone can operate) at a minimum ethylene partial pressure of 5 psi (34.5 kPa), 50 psi (345 kPa), 100 psi (689 kPa), 150 psi (1.03 MPa), 250 psi (1.72 MPa), or 500 psi (3.5 MPa); alternatively or additionally, at a maximum ethylene partial pressure of 2,500 psi (17.2 MPa), 2,000 psi (13.8 MPa), 1,500 psi (10.3 MPa), 1250 psi (8.62 MPa), or 1000 psi (6.89 MPa). In an embodiment, the oligomer product can be formed (or the reaction zone can operate) at an ethylene partial pressure ranging from any minimum ethylene partial pressure disclosed herein to any maximum ethylene partial pressure disclosed herein. In some non-limiting embodiments, the oligomer product can be formed (or the reaction zone can operate) at an ethylene partial pressure from 5 psi (34.5 kPa) to 2,500 psi (17.2 MPa), from 5 psi (34.5 kPa) to 2,000 psi (13.8 MPa), from 50 psi (345 kPa) to 2,000 psi (13.8 MPa), from 100 psi (689 kPa) to 2,000 psi (13.8 MPa), from 100 psi (689 kPa) to 1,500 psi (10.3 MPa), from 150 psi (1.03 MPa) to 1250 psi (8.62 MPa), from 250 psi (1.72 MPa) to 1000 psi (6.89 MPa), or from 500 psi (3.5 MPa) to 1000 psi (6.89 MPa). Other ethylene partial pressure ranges are readily apparent to those skilled in the art with the aid of this disclosure.

In an embodiment, the oligomer product can be formed (or the reaction zone can operate) at a minimum ethylene concentration of 4 mass %, 10 mass %, 25 mass %, 35 mass %, or 40 mass % based upon the total mass in the reaction zone; alternatively or additionally, at a maximum ethylene concentration of 70 mass %, 65 mass %, 60 mass %, 55 mass %, 50 mass %, or 48 mass % based upon the total mass in the reaction zone. In an embodiment, the oligomer product can be formed (or the reaction zone can operate) at an ethylene concentration ranging from any minimum ethylene concentration disclosed herein to any maximum ethylene concentration disclosed herein. In some non-limiting embodiments, the oligomer product can be formed (or the reaction zone can operate) at an ethylene concentration in a range of from 4 mass % to 70 mass %, from 4 mass % to 65 mass %, from 10 mass % to 60 mass %, from 25 mass % to 60 mass %, from 25 mass % to 55 mass %, from 35 mass % to 50 mass %, or from 40 mass % to 48 mass % based upon the total mass in the reaction zone. Other ethylene concentration ranges that can be utilized are readily apparent to those skilled in the art with the aid of this disclosure.

In an embodiment, the oligomer product can be formed (or the reaction zone can operate) at a minimum ethylene:chromium mass ratio of 50,000:1, 150,000:1, 250,000:1, or 400,000:1; alternatively, or additionally, at a maximum ethylene:chromium mass ratio of 5,000,000:1, 2,500,000:1, 1,500,000:1, or 1,000,000:1. In an embodiment, the oligomer product can be formed (or the reaction zone can operate) at an ethylene:chromium mass ratio ranging from any minimum ethylene:chromium mass ratio disclosed herein to any maximum ethylene:chromium mass ratio disclosed herein. In some non-limiting embodiments, the oligomer product can be formed (or the reaction zone can operate) at an ethylene:chromium mass ratio in the range of 50,000:1 to 5,000,000:1, 150,000:1 to 2,500,000:1, 250,000:1 to 1,500,000:1, or 400,000:1 to 1,000,000:1. Other ethylene:chromium mass ratio ranges that can be utilized are readily apparent to those skilled in the art with the aid of this disclosure. Generally, the ethylene:chromium mass ratio is based upon the chromium in the perfluorohydrocarbyl-$N^2$-phosphinyl amidine chromium salt complex having structure PFHNPACr I (or alternatively, the chromium salt).

In an embodiment wherein hydrogen is utilized, the oligomer product can be formed (or the reaction zone can operate) at a minimum hydrogen partial pressure of 1 psi (6.9 kPa), 2 psi (14 kPa), 5 psi (34 kPa), 10 psi (69 kPa), or 15 psi (103 kPa); alternatively or additionally at a maximum hydrogen partial pressure of 200 psi (1.4 MPa), 150 psi (1.03 MPa), 100 psi (689 kPa), 75 psi (517 kPa), or 50 psi (345 kPa). In an embodiment, the oligomer product can be formed (or the reaction zone can operate) at a hydrogen partial pressure ranging from any minimum hydrogen partial pressure disclosed herein to any maximum hydrogen partial pressure disclosed herein. In some non-limiting embodiments, wherein hydrogen is utilized, the oligomer product can be formed (or the reaction zone can operate) at a hydrogen partial pressure from 1 psi (6.9 kPa) to 200 psi (1.4 MPa), from 2 psi (14 kPa) to 150 psi (1.03 MPa), from 5 psi (34 kPa) to 100 psi (689 kPa), from 10 psi (69 kPa) to 75 psi (517 kPa), or from 15 psi (103 kPa) to 50 psi (345 kPa). Other hydrogen partial pressure ranges that can be utilized are readily apparent to those skilled in the art with the aid of this disclosure.

In an embodiment wherein hydrogen is utilized, the oligomer product can be formed (or the reaction zone can operate) at a minimum hydrogen to ethylene mass ratio of (0.05 g hydrogen)/(kg ethylene), (0.1 g hydrogen)/(kg ethylene), (0.25 g hydrogen)/(kg ethylene), (0.4 g hydrogen)/(kg ethylene), or (0.5 g hydrogen)/(kg ethylene); alternatively or additionally, at a maximum hydrogen to ethylene mass ratio of (5 g hydrogen)/(kg ethylene), (3 g hydrogen)/(kg ethylene), (2.5 g hydrogen)/(kg ethylene), (2 g hydrogen)/(kg ethylene), or (1.5 g hydrogen)/(kg ethylene). In an embodiment, the oligomer product can be formed (or the reaction zone can operate) at a hydrogen to ethylene mass ratio ranging from any minimum hydrogen to ethylene mass ratio disclosed herein to any maximum hydrogen to ethylene mass ratio disclosed herein. In some non-limiting embodiments, the oligomer product can be formed (or the reaction zone can operate) at a hydrogen to ethylene mass ratio from (0.05 g hydrogen)/(kg ethylene) to (5 g hydrogen)/(kg ethylene), from (0.1 g hydrogen)/(kg ethylene) to (5 g hydrogen)/(kg ethylene), from (0.25 g hydrogen)/(kg ethylene) to (4 g hydrogen)/(kg ethylene), from (0.4 g hydrogen)/(kg ethylene) to (3 g hydrogen)/(kg ethylene), from (0.4 g hydrogen)/(kg ethylene) to (2.5 g hydrogen)/(kg ethylene), from (0.4 g hydrogen)/(kg ethylene) to (2 g hydrogen)/(kg ethylene), from (0.5 g hydrogen)/(kg ethylene) to (2 g hydrogen)/(kg ethylene), or from (0.5 g hydrogen)/(kg ethylene) to (1.5 g hydrogen)/(kg ethylene). Other hydrogen to ethylene mass ratio ranges that can be utilized are readily apparent to those skilled in the art with the aid of this disclosure.

In an embodiment, the oligomer product can be formed (or the reaction zone can operate) at a minimum hydrogen:chromium of the perfluorohydrocarbyl-$N^2$-phosphinyl amidine chromium salt complex having structure PFHNPACr I (or alternatively, the chromium salt) mass ratio (minimum hydrogen:chromium mass ratio) of 1:1, 50:1, 100:1, or 200:1; alternatively or additionally, at a maximum hydrogen:chromium of the perfluorohydrocarbyl-$N^2$-phosphinyl amidine chromium salt complex having structure PFHNPACr I (or alternatively, the chromium salt) mass ratio (maximum hydrogen:chromium mass ratio) of 100,000:1, 50,000:1, 10,000:1, or 3,000:1. In an embodiment, the oligomer product can be formed (or the reaction zone can operate) at a hydrogen:chromium of the perfluorohydrocarbyl-$N^2$-phosphinyl amidine chromium salt complex having structure PFHNPACr I (or alternatively, the chromium salt) mass ratio (hydrogen:chromium mass ratio) ranging from any minimum hydrogen:chromium mass ratio disclosed herein to any maximum hydrogen:chromium mass ratio disclosed herein. In some non-limiting embodiments, the oligomer product can be formed (or the reaction zone can operate) at a hydrogen:chromium mass ratio in the range of 1:1 to 100,000:1, 50:1 to 50,000:1, 100:1 to 10,000:1, or 200:1 to 3,000:1. Other hydrogen:chromium mass ratio ranges that can be utilized are readily apparent to those skilled in the art with the aid of this disclosure. Generally, the hydrogen:chromium mass ratio is based upon the chromium in the perfluorohydrocarbyl-$N^2$-phosphinyl amidine chromium salt complex having structure PFHNPACr I (or alternatively, the chromium salt).

In an embodiment, the oligomer product can be formed (or the reaction zone can operate) at a minimum temperature of 0° C., 25° C. 40° C., or 50° C.; alternatively, or additionally, at a maximum temperature of 200° C., 150° C., 100° C., or 90° C. In an embodiment, the oligomer product can be formed (or the reaction zone can operate) at a temperature ranging from any minimum temperature disclosed herein to any maximum temperature disclosed herein. In some non-limiting embodiments, the oligomer product can be formed (or the reaction zone can operate) at a temperature from 0° C. to 200° C., from 25° C. to 150° C., from 40° C. to 100° C., from 50° C. to 100° C. or from 50° C. to 90° C. Other temperature ranges that can be utilized are readily apparent to those skilled in the art with the aid of this disclosure.

The reaction time (or residence time or average residence time) in the reaction zone can comprise any time that can produce the desired quantity of oligomer product, alternatively, any reaction time (or residence time) that can provide a desired catalyst system productivity; alternatively, any reaction time (or residence time or average residence time) that can provide a desired ethylene conversion. Relating to forming the oligomer product, the oligomer product can be formed over a period of time (or an average residence time) that can produce the desired quantity of olefin product or polymer product, provide the desired catalyst system productivity, and/or provide the desired conversion of monomer. In some embodiments, the reaction time (or residence time or average residence time) can range from 1 minute to 5 hours; alternatively, can range from 5 minutes to 2.5 hours; alternatively, can range from 10 minutes to 2 hours; or alternatively, can range from 15 minutes to 1.5 hours. In some embodiments (in continuous process embodiments), the reaction time (or residence time or average residence time) can be stated as an average reaction time (or average residence time) and can range from 1 minute to 5 hours; alternatively, can range from 5 minutes to 2.5 hours; alternatively, can range from 10 minutes to 2 hours; or alternatively, can range from 15 minutes to 1.5 hours.

In an embodiment, the processes described herein can have an ethylene conversion of at least 30%, 35%, 40%, or 45%. In another embodiment, the ethylene conversion can be a single pass conversion of at least 30%, 35%, 40%, or 45%.

In an embodiment, the processes described herein can have a catalyst system productivity of greater than 10,000 grams, 50,000 grams, 100,000 grams, 150,000 grams, 200,000 grams, 300,000 grams, or 400,000 grams ($C_6+C_8$) per gram of chromium (g ($C_6+C_8$)/g Cr).

Depending upon the catalyst system utilized, the processes described herein can be an ethylene oligomerization process, an ethylene trimerization process, an ethylene tetramerization process, or an ethylene trimerization and tetramerization process; alternatively, an ethylene oligomerization process; alternatively, an ethylene trimerization process; alternatively, an ethylene tetramerization process; or alternatively an ethylene trimerization and tetramerization process. In ethylene trimerization aspects and/or embodiments, the oligomer product can comprise at least 70 wt. % hexenes, at least 75 wt. % hexenes, at least 80 wt. % hexenes, at least 85 wt. % hexenes, or at least 90 wt. % hexenes based upon the weight of the oligomer product. In some ethylene trimerization aspects and/or embodiments, the oligomer product can comprise from 70 wt. % to 99.8 wt. % hexenes, from 75 wt. % to 99.7 wt. % hexenes, or from 80 wt. % to 99.6 wt. % hexenes based upon the weight of the oligomer product. In ethylene tetramerization aspects and/or embodiments, the oligomer product can comprise at least 70 wt. % octenes, at least 75 wt. % octenes, at least 80 wt. % octenes, at least 85 wt. % octenes, or at least 90 wt. % octenes based upon the weight of the oligomer product. In some ethylene tetramerization aspects and/or embodiments, the oligomer product can comprise from 70 wt. % to 99.8 wt. % octenes, from 75 wt. % to 99.7 wt. % octenes, or from 80 wt. % to 99.6 wt. % octenes based upon the weight of the oligomer product. In ethylene trimerization and tetramerization aspects and/or embodiments, the oligomer product can comprise at least 70 wt. % hexenes and octenes, at least 75 wt. % hexenes and octenes, at least 80 wt. % hexenes and octenes, at least 85 wt. % hexenes and octenes, or at least 90 wt. % hexenes and octenes based upon the weight of the oligomer product. In some ethylene trimerization and tetramerization aspects and/or embodiments, the oligomer product can comprise from 70 wt. % to 99.8 wt. % hexenes and octenes, from 75 wt. % to 99.7 wt. % hexenes and octenes, or from 80 wt. % to 99.6 wt. % hexenes and octenes based upon the weight of the oligomer product.

In ethylene oligomerization, ethylene trimerization, or ethylene trimerization and tetramerization aspects and/or embodiments, the ethylene trimer can comprise at least 90 wt. % 1-hexene; alternatively, at least 92.5 wt. % 1-hexene; alternatively, at least 95 wt. % 1-hexene; alternatively, at least 97 wt. % 1-hexene; or alternatively, at least 98 wt. % 1-hexene by weight of the ethylene trimer. In other ethylene oligomerization, ethylene trimerization, or ethylene trimerization and tetramerization aspects and/or embodiments, the ethylene trimer can comprise from 85 wt. % to 99.9 wt. % 1-hexene; alternatively, from 87.5 wt. % to 99.9 wt. % 1-hexene; alternatively, from 90 wt. % to 99.9 wt. % 1-hexene; alternatively, from 92.5 wt. % to 99.9 wt. % 1-hexene; alternatively, from 95 wt. % to 99.9 wt. % 1-hexene; alternatively, from 97 wt. % to 99.9 wt. % 1-hexene; or alternatively, from 98 wt. % to 99.9 wt. % 1-hexene by weight of the ethylene trimer.

In ethylene oligomerization, ethylene tetramerization, or ethylene trimerization and tetramerization aspects and/or embodiments, the ethylene tetramer can comprise at least 85 wt. % 1-octene; alternatively, at least 90 wt. % 1-octene; alternatively, at least 92.5 wt. % 1-octene; alternatively, at least 95 wt. % 1-octene; alternatively, at least 97 wt. % 1-octene; or alternatively, at least 98 wt. % 1-octene by weight of the ethylene tetramer. In other ethylene oligomerization, ethylene tetramerization, or ethylene trimerization and tetramerization aspects and/or embodiments, the ethylene tetramer can comprise from 85 wt. % to 99.9 wt. % 1-octene; alternatively, from 90 wt. % to 99.9 wt. % 1-octene; alternatively, from 92.5 wt. % to 99.9 wt. % 1-octene; alternatively, from 95 wt. % to 99.9 wt. % 1-octene; alternatively, from 97 wt. % to 99.9 wt. % 1-octene; or alternatively, from 98 wt. % to 99.9 wt. % 1-octene by weight of the ethylene tetramer.

In some aspects and/or embodiments, the processes described herein utilizing the perfluorohydrocarbyl-$N^2$-phosphinyl amidine having structure PFHNPA I or the $N^2$-phosphinyl amidine chromium salt complex having structure PFHNPACr I can produce an oligomer product comprising a mixture of $C_8$ and $C_6$ olefin products wherein the mass ratio of $C_8$ olefin products to $C_6$ olefin products can be at least 1.5:1, at least 2:1, at least 3:1, at least 5:1, or at least 10:1.

EXAMPLES

Methodology

Development of accurate density-functional theory (DFT), solvation methods, and quantum mechanical tools have emerged that can enable prediction of products from molecular catalysts. One area of interest is to be able to predict the relative amounts of hexenes and/or octenes produced by an ethylene trimerization and/or tetramerization catalyst system. To be able to use computational methods to predict the relative amounts of hexenes and/or octenes produced by a particular ethylene trimerization and/or tetramerization catalyst, a plausible mechanism capable of demonstrating hexenes and/or octenes selectivity is needed. Using computational and experimental studies of i) Britovsek, G. J. P, and McGuinness, D. S. Chem. Eur. J. 2016, 22, 16891-16896, ii) Britovsek, G. J. P.; McGuinness, D. S.; Tomov, A. K. Catal. Sci. Technol. 2016, 6, 8234-8241, iii) Hossain, M. A.; Kim, H. S.; Houk, K. N. Cheong, M. Bull. Korean Chem. Soc. 2014, 35, 2835-2838, iv) Gong, M.; Liu, Z.; Li, Y.; Ma, Y.; Sun, Q.; Zhang, J.; Liu, B. Organometallics 2016, 35, 972-981, v) Yang, Y.; Liu, Z.; Cheng, R.; He, X.; Liu, B. Organometallics 2014, 33, 2599-2607, vi) Qi, Y.; Zhong, L.; Liu. Z.; Qiu, P.; Cheng, R.; He, X.; Vanderbilt, J.; Liu, B. Organometallics 2010, 29, 1588-1602, vii) Budzelaar, P. H. M. Can. J. Chem. 2009, 87, 832-837, viii) Bhaduri, S.; Mukhopadhyay, S.; Kulkarni, S. A. J. Organomet. Chem. 2009, 694, 1297-1307, and ix) van Rensburg, W. J.; Grové, C.; Stevnberg, J. P.; Stark, K. B.; Huyser, J. J.; Steynberg, P. J. Organometallics 2004, 23, 1207-1222, and experimental studies of Bartlett, S. A.; Moulin, J.; Tromp, M.; Reid, G.; Dent, A. J.; Cibin, G.; McGuinness, D. S.; Evans, J. ACS Catal. 2014, 4, 4201-4204, and without being limited by theory, Scheme 1 was developed as a plausible catalytic mechanism for ethylene trimerization and/or tetramerization.

Scheme 1

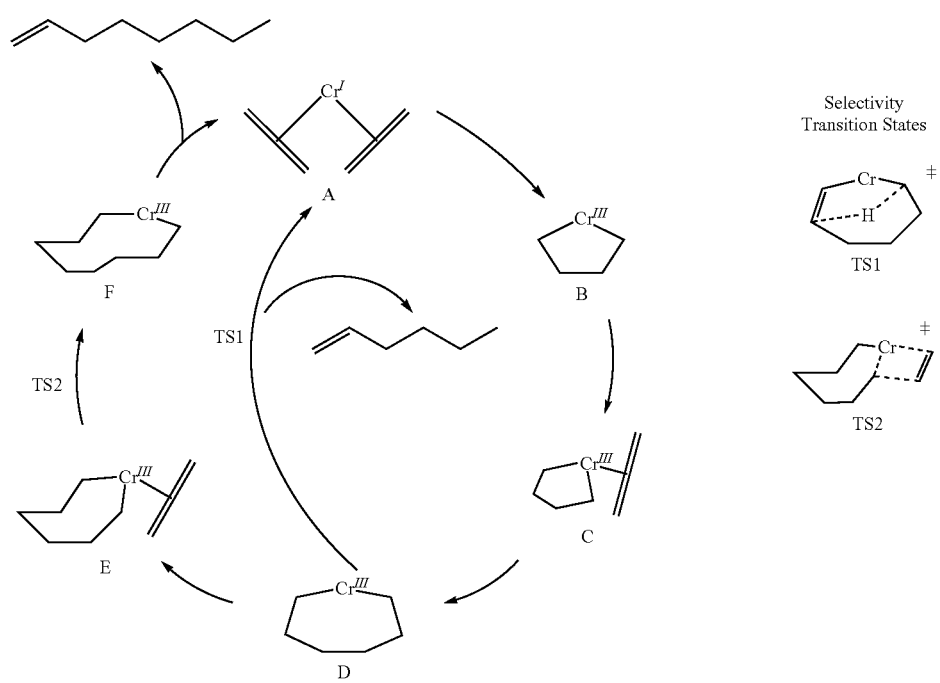

In Scheme 1, precatalyst activation in the presence of ethylene can generate a low-valent Cr ethylene coordination species A. Oxidative C—C bond coupling of the two ethylene units can form chromacyclopentane B which can then coordinate with another ethylene to form the chromacyclopentane ethylene coordination species C followed by migratory ethylene insertion which can lead to the chromacycloheptane intermediate D. Intermediate D represents the common intermediate in the mechanistic paths where the mechanisms for producing hexenes and octenes can diverge. Hexenes can be produced from the chromacycloheptane intermediate D by β-hydrogen transfer via transition state TS1 to form 1-hexene and a reduced Cr species which can then reform, in the presence of ethylene, the low-valent Cr ethylene coordination species A. Octenes can be produced from the chromacycloheptane intermediate D by i) ethylene coordination to form the ethylene coordinated species E, ii) migratory insertion of ethylene through transition state TS2 to form the chromacyclononane species F, and iii) β-hydrogen transfer within chromacyclononane species F to produce 1-octene and a reduced Cr species which can then reform, in the presence of ethylene, the low-valent Cr ethylene coordination species A. This two-transition state model assumes dynamic equilibrium, often known as Curtin-Hammett conditions, where TS1 and TS2 arise from the common chromacycloheptane intermediate D and a fast equilibrium of possible intermediates leading up to TS1 and TS2. Via this mechanism selectivity can result from competitive β-hydrogen transfer of transition state TS1 and the migratory ethylene insertion from intermediate D through transition state TS2.

Without being limited by theory, the mechanism in Scheme 1 was then applied in a predictive method to allow for prediction of the relative amounts of hexenes and/or octenes for previously unknown $N^2$-phosphinyl amidine chromium salt complexes; for example, the herein disclosed perfluoro-$N^2$-phosphinyl amidine chromium salt complexes having structure PFHNPACr I. In this predictive method, Density Functional Theory calculations were applied to experimentally evaluated $N^2$-phosphinyl amidine chromium salt complexes to provide a correlation between the Density Functional Theory calculations and the experimentally observed amounts of hexenes and/or octenes. The correlation was then used to predict the amounts of hexenes and/or octenes produced by the herein disclosed $N^2$-phosphinyl amidine chromium salt complexes having structure PFHNPACr I.

Without wishing to be limited by theory, Scheme 2 illustrates the critical competing and selectivity determining reaction coordinate pathways for producing hexenes and octenes including the general $N^2$-phosphinyl amidine chromium chromacycloheptane complex CrCH 1, the general $N^2$-phosphinyl amidine chromium chromacycloheptane complex CrCH 2, the general $N^2$-phosphinyl amidine chromium salt complex hexene transition state TS C6, and the general $N^2$-phosphinyl amidine chromium salt complex octene transition state TS C8. Thus, for catalyst systems based upon general $N^2$-phosphinyl amidine chromium salt complexes, the Gibbs free energy difference, $\Delta\Delta G^{\ddagger}$, between: 1) the difference in the Gibbs free energy of the general $N^2$-phosphinyl amidine chromium chromacycloheptane complex CrCH 1 and the general $N^2$-phosphinyl amidine chromium salt complex hexene transition state TS C6; and 2) the difference in the Gibbs free energy of the general $N^2$-phosphinyl amidine chromium chromacycloheptane complex CrCH 2 and the general $N^2$-phosphinyl amidine chromium salt complex Scheme 2

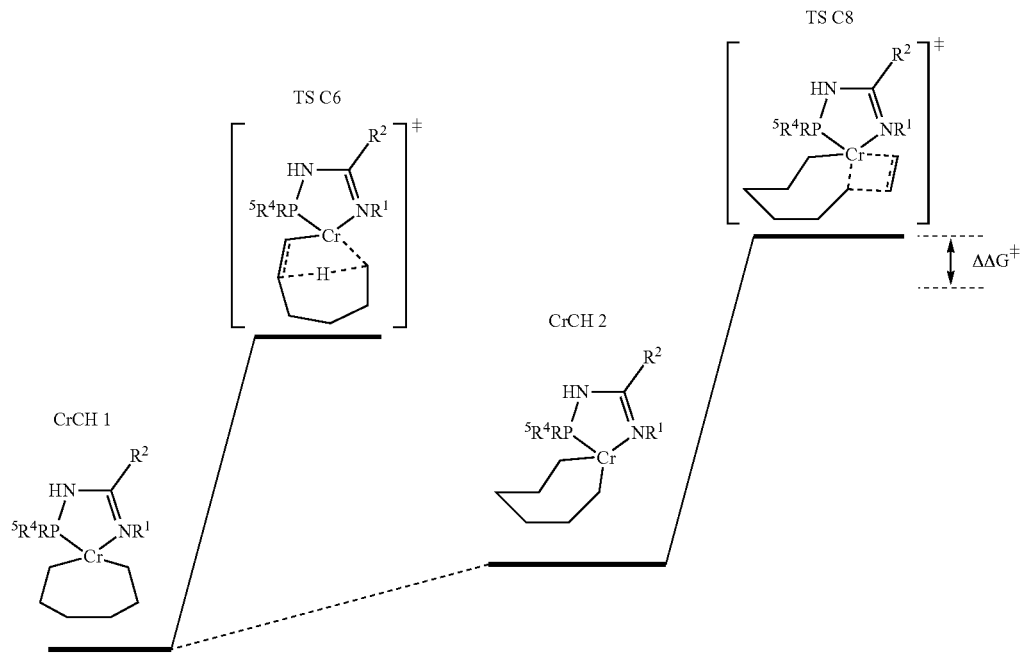

octene transition state TS C8 can be utilized in a predictive correlative method to predict the relative amounts of hexenes and/or octenes produced by an $N^2$-phosphinyl amidine chromium salt complex, e.g., a $N^2$-phosphinyl amidine chromium salt complex having the structure shown in Scheme 2 wherein $R^1$, $R^2$, $R^4$, and $R^5$ all are $CF_3$ (trifluoromethane). Further, and without being limited by theory, since the general $N^2$-phosphinyl amidine chromium chromacycloheptane complex CrCH 1 and the general $N^2$-phosphinyl amidine chromium chromacycloheptane complex CrCH 2 are carbon-carbon chromacycloheptane rotational isomers of each other and it is expected that there is a low energy barrier for their interconversion, the calculation of the Gibbs free energy difference, $\Delta\Delta GI$, can be simplified to the calculation of the Gibbs free energy difference between the general $N^2$-phosphinyl amidine chromium salt complex hexene transition state TS C6 and the general $N^2$-phosphinyl amidine chromium salt complex octene transition state TS C8 ($\Delta\Delta GI$, in Scheme 2). Thus, the Gibbs free energy difference $\Delta\Delta G$ was correlated with the experimentally observed amounts of hexenes and/or octenes produced by the experimentally tested $N^2$-phosphinyl amidine chromium salt complexes.

Density Functional Theory Calculations

Density Functional Theory calculations (specifically, unrestricted UM06L/Def2-TZVP/UM06/6-31G(d,p) (LANL2DZ) theory) combined with the SMD implicit solvent model for cyclohexane (as implemented in Marenich, A. V.; Cramer, C. J.; Truhlar, D. G., *J. Phys. Chem. B.* 2009, 113, 6378-6396) was used to calculate the Gibbs free energy of the cationic $N^2$-phosphinyl amidine chromium salt complex hexene transition state TS C6 (hereafter $N^2$-phosphinyl amidine chromium salt complex hexene transition state TS C6) and the cationic $N^2$-phosphinyl amidine chromium salt complex octene transition state TS C8 (hereafter $N^2$-phosphinyl amidine chromium salt complex hexene transition state TS C8) and, for each $N^2$-phosphinyl amidine chromium salt complex. The Gibbs free energy difference between the $N^2$-phosphinyl amidine chromium salt complex hexene transition state TS C6 and the $N^2$-phosphinyl amidine chromium salt complex octene transition state TS C8, $\Delta\Delta G^{\ddagger}$, for each $N^2$-phosphinyl amidine chromium salt complex was then calculated. The calculations of the Gibbs free energy of the cationic $N^2$-phosphinyl amidine chromium salt complex hexene transition state TS C6 (and other transition state energies used herein) and the cationic $N^2$-phosphinyl amidine chromium salt complex octene transition state TS C8 (and other transition state energies used herein) were performed without considering the impact of the balancing anion.

The density functional theory calculations were carried out using Gaussian 09 (Frisch, M. J. et al. *Gaussian* 09™, Revision B.01, Gaussian, Inc.: Wallingford, Conn., USA. 2009).

Geometries to account for each degree of freedom and each spin state for the $N^2$-phosphinyl amidine chromium salt complex hexene transition state TS C6 (3 to 40 conformations depending on the exact ligand) and the $N^2$-phosphinyl amidine chromium salt complex octene transition state TS C8 (3 to 40 conformation depending on the exact ligand) for each $N^2$-phosphinyl amidine chromium salt complex were calculated using the pseudopotential LANL2DZ basis set for chromium (integrated into the Gaussian 09™, Revision B.01) and the unrestricted approximation of local Minnesota 06 density functional theory 6-31G(d,p) basis set (i.e., UM06/6-31G(d,p) basis set) for all other atoms in the $N^2$-phosphinyl amidine chromium salt transition states. The transition-state structures with a complete set of force constants were calculated to ensure a single negative vibrational frequency that corresponded to the reaction coordinate. Additionally, the ground-state structure vibrational frequencies were calculated to correspond to the second-order energy derivatives (i.e., force constants) and were analyzed to confirm a local minimum energy structure. Additionally, zero point energies ($\Delta E_{ZPE(small)}$), vibrational, rotational, and translational energies ($\Delta U_{vib(small)}$, $\Delta U_{rot(small)}$, $\Delta U_{trans(small)}$, respectively), and vibrational, rotational, and translational entropies ($\Delta S_{vib(small)}$, $\Delta S_{rot(small)}$, $\Delta S_{trans(small)}$, respectively) were obtained to use in the calculation of the Gibbs free energy for the $N^2$-phosphinyl amidine chromium salt complex hexene transition state TS C6 and the $N^2$-phosphinyl amidine chromium salt complex octene transition state TS C8.

The solvated geometries for the $N^2$-phosphinyl amidine chromium salt complex hexene transition state TS C6 conformation having the lowest energy and the $N^2$-phosphinyl amidine chromium salt complex octene transition state TS C8 conformation having the lowest energy, along with any conformations having an energy relatively close to the $N^2$-phosphinyl amidine chromium salt complex hexene transition state TS C6 conformation having the lowest energy and the $N^2$-phosphinyl amidine chromium salt complex octene transition state TS C8 conformation having the lowest energy, were calculated using a continuum model (SMD) that was parametrized and implemented in Gaussian 09 for cyclohexane. The transition-state structures with a complete set of force constants were calculated to ensure a single negative vibrational frequency that corresponded to the reaction coordinate. Additionally, the ground-state structure vibrational frequencies were calculated to correspond to the second-order energy derivatives (i.e., force constants) and were analyzed to confirm a local minimum energy structure.

The total self-consistent field electronic energy containing the electron kinetic and potential energies, and nuclear repulsion energy ($E_{(large)}$) and the standard state solvation free energy change ($\Delta G_{solv(large)}$) for the $N^2$-phosphinyl amidine chromium salt complex hexene transition state TS C6 and the $N^2$-phosphinyl amidine chromium salt complex octene transition state TS C8 were then calculated using the unrestricted approximation of local Minnesota 06 density functional theory Def2-TZVP basis set UM06L/Def2-TZVP (downloaded from https://bse.pnl.gov/bse/portal on Jan. 1, 2016) to provide accurate spin state energies and accurate calculations for weak dispersion forces.

The Gibbs free energy of the $N^2$-phosphinyl amidine chromium salt complex hexene transition state TS C6 and the $N^2$-phosphinyl amidine chromium salt complex octene transition state TS C8 were then calculated using the equation $E_{(large)} + \Delta E_{ZPE(small)} + \Delta U_{vib(small)} + \Delta U_{rot(small)} + \Delta U_{trans(small)} + nRT - T\Delta S_{vib(small)} - T\Delta S_{rot(small)} - T\Delta S_{trans(small)} + \Delta G_{solv(large)}$ where R is the ideal gas constant and T is the temperature (298 K was used for these calculations). The Gibbs free energy difference, $\Delta\Delta G$, between the $N^2$-phosphinyl amidine chromium salt complex hexene transition state TS C6 and the $N^2$-phosphinyl amidine chromium salt complex octene transition state TS C8 for each $N^2$-phosphinyl amidine chromium salt complex was then calculated as the Gibbs free energy of the $N^2$-phosphinyl amidine chromium salt complex hexene transition state TS C6 minus the Gibbs free energy of the $N^2$-phosphinyl amidine chromium salt complex octene transition state TS C8.

Table 1 provides the calculated $\Delta\Delta G^{\ddagger}$ values between the $N^2$-phosphinyl amidine chromium salt complex hexene transition state TS C6 and the $N^2$-phosphinyl amidine chromium salt complex octene transition state TS C8 for five $N^2$-phosphinyl amidine chromium salt complexes (NPA 1-NPA 5) for which experimental data using a chromium complex having the indicated $N^2$-phosphinyl amidine ligand had been determined (see Ethylene Oligomerization Examples). Table 1 further provides predictive values of $\Delta\Delta G^{\ddagger}$ and product distribution for an $N^2$-phosphinyl amidine chromium salt complex using the ligand having structure CF3HNPA I.

Ethylene Oligomerizations Examples

A 1 L stainless steel autoclave reactor was dried under vacuum at 110° C. for at least 8 hours prior to use. The reactor was then cooled to 50° C. In a drybox, a 20 mL glass vial was charged with an N-phosphino amidine chromium complex (0.009-0.010 mmol), ethylbenzene (2.00 g), MMAO-3A (400-800 equivalents), Al (7 wt. % Al solution in heptanes), and an internal standard (n-nonane, 1.00 g). This solution was then added to a 0.5 L glass charger containing cyclohexane (400 mL). The combined solution was removed from the drybox and charged into the 1 L stainless steel autoclave reactor under static vacuum. The reactor was then heated to 5° C. below the reaction temperature and charged with hydrogen. Ethylene was then charged to the reactor on-demand to maintain the desired operating pressure. After 30 minutes, water cooling was applied to the 1 L stainless steel autoclave reactor to terminate the ethylene oligomerization reaction. When the reactor temperature reached 35° C. the unreacted ethylene and hydrogen gas was vented to the atmosphere. A liquid sample of the 1 L stainless steel autoclave reactor contents was then collected at room temperature and analyzed by gas chromatography. The reactor solids were collected by filtering the reaction and cleaning the reactor walls and cooling coil. The mass % of the trimer (1-hexene) and tetramer (1-octene) observed in the oligomer product (as a percentage of the total trimer and tetramer produced) for each of chromium salt complexes of $N^2$-phosphinyl amidine ligands 1-5 are reported in Table 1.

TABLE 1

| | Calculated Values | | | | Experimentally Observed Values | |
|---|---|---|---|---|---|---|
| Ligand† | $\Delta\Delta G^{\ddagger}$, kcal | Trimer, mass % | Tetramer, mass % | P—Cr—N Bond Angle, ° | Trimer, mass % | Tetramer, mass % |
| 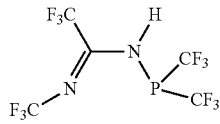 CF3HNPA I | −4.8 | 4.4 | 95.6 | 72 | ND | ND |

TABLE 1-continued
| Ligand[†] | Calculated Values | | | | Experimentally Observed Values | |
|---|---|---|---|---|---|---|
| | ΔΔG[‡], kcal | Trimer, mass % | Tetramer, mass % | P—Cr—N Bond Angle, ° | Trimer, mass % | Tetramer, mass % |
| 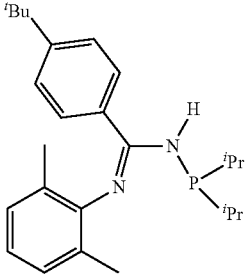 NPA 1 | 2.4 | 99.1 | 0.9 | 77 | 93.6 | 0.9 |
| 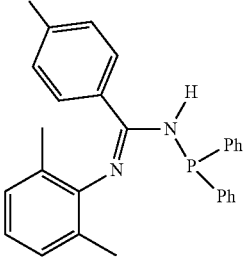 NPA 2 | −0.5 | 82.6 | 17.4 | 76 | 85.4 | 12 |
| 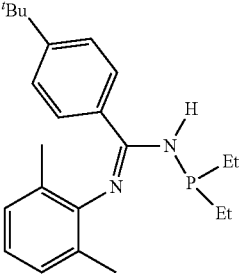 NPA 3 | −0.2 | 86.9 | 13.1 | 75 | 79.3 | 15 |
| 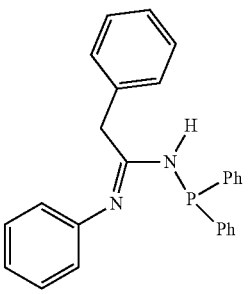 NPA 4 | −1.3 | 65.9 | 34.1 | 76 | 65.2 | 30.5 |

TABLE 1-continued

| Ligand[†] | Calculated Values | | | | Experimentally Observed Values | |
|---|---|---|---|---|---|---|
| | $\Delta\Delta G^{\ddagger}$, kcal | Trimer, mass % | Tetramer, mass % | P—Cr—N Bond Angle, ° | Trimer, mass % | Tetramer, mass % |
| 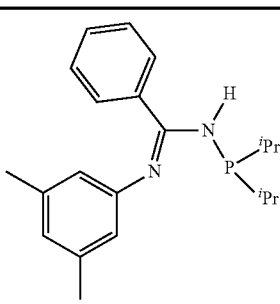<br>NPA 5 | −1.3 | 66.9 | 33.1 | 77 | 52.2 | 33.7 |

[†]tBu = tert-butyl, iPr = isopropyl, Ph = phenyl, Et = ethyl

Correlation of $\Delta\Delta G^{\ddagger}$ and $C_6/C_8$ Mass Ratio

The calculated $\Delta\Delta G^{\ddagger}$ for the experimentally evaluated chromium salt complexes of the $N^2$-phosphinyl amidine ligands NPA 1-NPA 5 were found to provide a good linear correlation with the natural logarithm of the $C_6$ to $C_8$ mass ratio, ln(mass $C_6$/mass $C_8$) (or alternatively ln($C_6/C_8$), observed when the chromium salt complexes of the five $N^2$-phosphinyl amidine ligands were utilized in a catalyst system for oligomerizing ethylene (see Ethylene Oligomerization Examples provided herein). FIG. 1 provides a graph of the calculated $\Delta\Delta G^{\ddagger}$ versus ln($C_6/C_8$) for the chromium salt complexes of the five $N^2$-phosphinyl amidine ligands in Table 1. The least squares fitted line of this data had a correlation coefficient, $R^2$, of 0.9744 indicating a good correlation between $\Delta\Delta GI$ and the experimentally observed mass of hexenes and octenes. Use of the $\Delta\Delta G^{\ddagger}$ versus ln($C_6/C_8$) trend line to calculate the ln($C_6/C_8$) for the chromium salt complex of the perfluoro-$N^2$-phosphinyl amidine ligand having structure CF3HNPA I gave a ln($C_6/C_8$) of −3.08 which corresponds to a 4.3 mass % $C_6$ and a 95.7 mass % of $C_8$. The mass % of a $C_6$ and $C_8$ are provided in Table 1.

Synthesis of $N^2$-phosphinyl Amidine Ligands

The synthesis of the $N^2$-phosphinyl amidine ligands (NPA 1-NPA 5) was, and the potential synthesis of the perfluoro-$N^2$-phosphinyl amidine ligand of the present disclosure (e.g., CF3HNPA 1) can be performed using the general synthetic procedures as provided in U.S. patent application Ser. No. 15/166,991 which is incorporated herein by reference in its entirety.

ADDITIONAL DISCLOSURE

Accordingly, the scope of protection is not limited by the description set out above but is only limited by the claims which follow, that scope including all equivalents of the subject matter of the claims. Each and every claim is incorporated into the specification as an aspect of the present disclosure. Thus, the claims are a further description and are an addition to the detailed description of the present disclosure. The disclosures of all patents, patent applications, and publications cited herein are hereby incorporated by reference.

Embodiment 1

A catalyst system comprising an $N^2$-phosphinylamidine chromium salt complex having Structure PFHNPACr I:

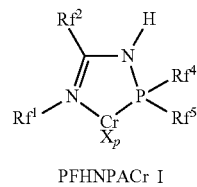

PFHNPACr I wherein $Rf^1$, $Rf^2$, $Rf^4$, and $Rf^5$ are independently selected from a perfluorohydrocarbyl group; and $CrX_p$ is a chromium salt where X is a monoanion, and p is an integer from 2 to 6.

Embodiment 2

The catalyst system of claim 1, further comprising an organoaluminum compound.

Embodiment 3

The catalyst system of claim 2, wherein the organoaluminum compound comprises an aluminoxane.

Embodiment 4

The catalyst system of claim 3, wherein the aluminoxane comprises methylaluminoxane (MAO), a modified methylaluminoxane, ethylaluminoxane, n-propylaluminoxane, iso-propylaluminoxane, n-butylaluminoxane, sec-butylaluminoxane, iso-butylaluminoxane, t-butyl aluminoxane, I-pentylaluminoxane, 2-pentylaluminoxane, 3-pentylaluminoxane, isopentylaluminoxane, neopentylaluminoxane, or mixtures thereof.

Embodiment 5

The catalyst system of any one of claims 2 to 4, where the catalyst system has an aluminum of the organoaluminum compound to chromium of the $N^2$-phosphinylamidine chromium salt complex molar ratio in the range of 10:1 to 5,000:1.

Embodiment 6

A process comprising:
a) contacting
  i) ethylene,
  ii) a catalyst system comprising an $N^2$-phosphinylamidine chromium salt complex having Structure PFHNPACr I:

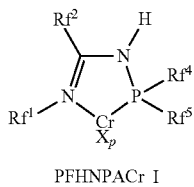

PFHNPACr I wherein $Rf^1$, $Rf^2$, $Rf^4$, and $Rf^5$ are independently selected from a perfluorohydrocarbyl group; and $CrX_p$ is a chromium salt where X is a monoanion and p is an integer from 2 to 6, and
  iii) optionally an organic reaction medium, and
b) forming an oligomer product in a reaction zone.

Embodiment 7

The process of claim 6, wherein the reaction zone has any temperature disclosed herein, e.g., at least 0° C., 25° C., 40° C., or 50° C., in a range of 0° C. to 200° C., 25° C. to 150° C., 40° C. to 100° C., 50° C. to 100° C., or 50° C. to 90° C., etc.

Embodiment 8

The process of any one of claim 6 or 7, wherein the reaction zone has any ethylene partial pressure disclosed herein, e.g., at least 5 psi (34.5 kPa), 50 psi (345 kPa), 250 psi (1.72 MPa), or 500 psi (3.5 MPa), in the range of 5 psi (34.5 kPa) to 2,500 psi (17.2 MPa), 5 psi (34.5 kPa) to 2,000 psi (13.8 MPa), 100 psi (689 kPa) to 2,000 psi (13.8 MPa), 150 psi (1.03 MPa) to 1500 psi (10.3 MPa), 250 psi (1.72 MPa) to 1250 psi (8.62 MPa), or 500 psi (3.5 MPa) to 1000 psi (6.89 MPa), etc.

Embodiment 9

The process of any one of claims 6 to 8, wherein the reaction zone has any minimum ethylene:chromium mass ratio disclosed herein, e.g., 50,000:1, 150.000:1, 250,000:1, or 400,000:1, in the range of 50,000:1 to 5,000,000:1, 150,000:1 to 2,500,000:1, 250,000:1 to 1,500,000:1, or 400,000:1 to 1,000,000:1.

Embodiment 10

The process of any one of claims 6 to 9, wherein the catalyst system further comprises an organoaluminum compound.

Embodiment 11

The process of claim 10, wherein the organoaluminum compound comprises, or consists essentially of, an aluminoxane.

Embodiment 12

The process of claim 11, wherein the aluminoxane comprises, or consists essentially of, methylaluminoxane (MAO), a modified methylaluminoxane, ethylaluminoxane, n-propylaluminoxane, isopropylaluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, isopentylaluminoxane, neopentylaluminoxane, or mixtures thereof.

Embodiment 13

The process of any one of claim 10 to 12, wherein the reaction zone has any aluminum of the organoaluminum compound to chromium of the $N^2$-phosphinylamidine chromium salt complex molar ratio disclosed herein, e.g., at least 10:1, 50:1, 75:1, or 100:1, in the range of 10:1 to 5,000:1, 50:1 to 3,000:1, 50:1 to 3,000:1, 75:1 to 2,000:1, 100:1 to 2,000:1, or 100:1 to 1,000:1, etc.

Embodiment 14

The process of any one of claims 6 to 13, wherein the process includes the organic reaction medium.

Embodiment 15

The process of claim 14, wherein the reaction zone has any chromium of the $N^2$-phosphinylamidine chromium salt complex concentration disclosed herein, e.g., at least $1\times10^{-5}$ Cr equivalents/liter, $1\times10^{-5}$ Cr equivalents/liter, or $5\times10^{-4}$ Cr equivalents/liter, in the range of $1\times10^{-6}$ Cr equivalents/liter to 1 Cr equivalents/liter, $1\times10^{-5}$ Cr equivalents/liter to 0.5 Cr equivalents/liter, $5\times10^{-4}$ Cr equivalents/liter to 0.1 Cr equivalents/liter, etc.

Embodiment 16

The process of claim 14 or 15, wherein the reaction zone has any ethylene concentration disclosed herein, e.g., at least 4 mass %, 10 mass %, 25 mass %, 35 mass %, or 40 mass %, in the range of 4 mass % to 70 mass %, 4 mass % to 60 mass %, 10 mass % to 60 mass %, 25 mass % to 55 mass %, 35 mass % to 50 mass %/, or 40 mass % to 48 mass %, etc. based upon the total mass in the reaction zone.

Embodiment 17

The process of any one of claims 6 to 16, wherein the process further comprises contacting hydrogen with the ethylene, the catalyst system, and/or the optional organic reaction medium.

Embodiment 18

The process of claim 17, wherein the reaction zone has any hydrogen partial pressure disclosed herein, e.g., at least 1 psi (6.9 kPa), 2 psi (14 kPa), 5 psi (34 kPa), 10 psi (69 kPa), or 15 psi (103 kPa), in the range of 1 psi (6.9 kPa) to 200 psi (1.4 MPa), 5 psi (34 kPa) to 100 psi (689 kPa), 10 psi (69 kPa) to 75 psi (517 kPa), or 15 psi (100 kPa) to 50 psi (345 kPa), etc.

Embodiment 19

The process of claim 17 or 18, wherein the reaction zone has any hydrogen to ethylene mass ratio disclosed herein, e.g., at least (0.05 g hydrogen)/(kg ethylene), (0.1 g hydrogen)/(kg ethylene), (0.25 g hydrogen)/(kg ethylene), (0.4 g hydrogen)/(kg ethylene), or (0.5 g hydrogen)/(kg ethylene), in the range of (0.05 g hydrogen)/(kg ethylene) to (5 g hydrogen)/(kg ethylene), (0.1 g hydrogen)/(kg ethylene) to (5 g hydrogen)/(kg ethylene), (0.25 g hydrogen)/(kg ethylene) to (4 g hydrogen)/(kg ethylene), (0.4 g hydrogen)/(kg ethylene) to (3 g hydrogen)/(kg ethylene), (0.4 g hydrogen)/(kg ethylene) to (2.5 g hydrogen)/(kg ethylene), (0.4 g hydrogen)/(kg ethylene) to (2 g hydrogen)/(kg ethylene), or (0.5 g hydrogen)/(kg ethylene) to (1.5 g hydrogen)/(kg ethylene), etc.

Embodiment 20

The process of claim 17, 18 or 19, wherein the reaction zone has any hydrogen:chromium mass ratio disclosed herein, e.g., at least 1:1, 50:1, 100:1, or 200:1, in the range of 1:1 to 100,000:1, 50:1 to 50,000:1, 100:1 to 10,000:1, or 200:1 to 3,000:1, etc.

Embodiment 21

The process of any one of claims 6 to 20, wherein a $C_6$ oligomer product has any 1-hexene content disclosed herein, e.g., at least 90 wt. %, at least 92.5 wt. %, at least 95 wt. %, at least 97 wt. %, or at least 98 wt. % 1-hexene, from 85 wt. % to 99.9 wt. %, from 87.5 wt. % to 99.9 wt. %, from 90 wt. % to 99.9 wt. %, from 92.5 wt. % to 99.9 wt. %, from 95 wt. % to 99.9 wt. %, from 97 wt. % to 99.9 wt. %, or from 98 wt. % to 99.9 wt. % 1-hexene, etc.

Embodiment 22

The process of any one of claims 6 to 21, wherein a $C_8$ oligomer product has any 1-octene content disclosed herein, e.g., at least 90 wt. %, at least 92.5 wt. %, at least 95 wt. %, at least 97 wt. % 1-octene, or at least 98 wt. % 1-octene, from 90 wt. % to 99.9 wt. %, from 92.5 wt. % to 99.9 wt. %, from 95 wt. %0 to 99.9 wt. %, from 97 wt. % to 99.9 wt. %, or from 98 wt. %0 to 99.9 wt. % 1-octene, etc.

Embodiment 23

The process of any one of claims 6 to 22, wherein the oligomer product has any $C_8/C_6$ ratio disclosed herein, e.g., at least 1.5:1, at least 2:1, at least 3:1, at least 5:1, or at least 10:1, etc.

Embodiment 24

The subject matter of any one of claims 1 to 23, wherein the perfluorohydrocarbyl groups are independently selected from a $C_1$ to $C_{10}$ perfluorohydrocarbyl group, a $C_1$ to $C_{15}$ perfluorohydrocarbyl group, or a $C_1$ to $C_{10}$ perfluorohydrocarbyl group.

Embodiment 25

The subject matter of any one of claims 1 to 23, wherein the $Rf^1$, $Rf^2$, $Rf^4$, and $Rf^5$ are independently selected from any trifluoromethyl substituted phenyl group disclosed herein, e.g., a mono-trifluoromethylphenyl group, a di-trifluoromethylphenyl group, or tri-trifluoromethylphenyl group, or a 2-trifluoromethylphenyl group, a 2,6-di-trifluoromethylphenyl group, a 3,5-di-trifluoromethylphenyl group, or a 2,4,6-tri-trifluoromethylphenyl group.

Embodiment 26

The subject matter of any one of claim 1 to 23 wherein, the perfluorhydrocarbyl groups i) are independently selected from a perfluoroalkyl group or a perfluoroaryl group; ii) are independently selected from a perfluoroalkyl group; or iii) are independently selected from a perfluoroaryl group.

Embodiment 27

The subject matter of any one of claims 1 to 23, wherein $Rf^1$, $Rf^2$, $Rf^4$, and $Rf^5$ are independently selected from any perfluoroalkyl group disclosed herein, e.g., a $C_1$ to $C_{20}$ perfluoroalkyl group, a $C_1$ to $C_{10}$ perfluoroalkyl group, or a $C_1$ to $C_5$ perfluoroalkyl group, etc.

Embodiment 28

The subject matter of claim 27, wherein the perfluoroalkyl groups are independently selected from a trifluoromethyl group, a 1,1, difluoroethyl group, or a pentafluoroethyl group.

Embodiment 29

The subject matter of any one of claims 1 to 23, wherein $Rf^1$, $Rf^2$, $Rf^4$, and $Rf^5$ are independently selected from any perfluoroaryl group disclosed herein e.g., a $C_6$ to $C_{20}$ perfluoroaryl group, a $C_6$ to $C_{15}$ perfluoroaryl group, or a $C_6$ to $C_{10}$ perfluoroaryl group, etc.

Embodiment 30

The subject matter of claim 29, wherein $Rf^1$, $Rf^2$, $Rf^4$, and $Rf^4$ are independently selected from any perfluorophenyl group disclosed herein; e.g., a $C_6$ to $C_{20}$ perfluorophenyl group, a $C_6$ to $C_{15}$ perfluorophenyl group, or a $C_6$ to $C_{10}$ perfluorophenyl group, etc.

Embodiment 31

The subject matter of claim 30, wherein the perfluorophenyl groups are independently selected from a 2,4-difluorophenyl group, a 2,5-diflurophenyl group, a 3,5, difluorophenyl group, a 2,4,6-trifluorophenyl group, or a 2,3,4,5,6-pentafluorophenyl group.

Embodiment 32

The subject matter of any one of claims 1 to 23 or 27, wherein the $N^2$-phosphinylamidine chromium salt complex has the structure:

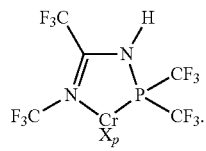

Embodiment 33

The subject matter of any one of claims 1 to 32, wherein the chromium salt is a chromium(III) carboxylate, a chromium(III) β-diketonate, or a chromium(III) halide.

Embodiment 34

The subject matter of any one of claims 1 to 32, wherein the chromium salt is a chromium (III) chloride.

All publications and patents mentioned herein are hereby incorporated in their entirety by reference into the present disclosure. The publications and patents mentioned herein can be utilized for the purpose of describing and disclosing, for example, the constructs and methodologies that are described in the publications, which might be used in connection with the presently described subject matter. The publications discussed throughout the text are provided solely for their disclosure prior to the filing date of the present application. Nothing herein is to be construed as an admission that the inventors are not entitled to antedate such disclosure by virtue of the results of prior investigations, including but not limited to experimental results.

Therefore, the present disclosure is well adapted to attain the ends and advantages mentioned as well as those that are inherent therein. This concludes the detailed description. The particular embodiments disclosed above are illustrative only, as the subject matter of the present disclosure can be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above can be altered or modified and all such variations are considered within the scope and spirit of the subject matter of the present disclosure. Accordingly, the protection sought herein is as set forth in the claims herein.

What is claimed is:

1. A catalyst system comprising an $N^2$-phosphinylamidine chromium salt complex having Structure PFHNPACr I:

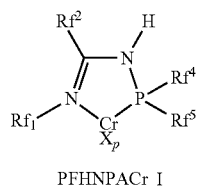

PFHNPACr I wherein $Rf^1$, $Rf^2$, $Rf^4$, and $Rf^5$ are independently selected from a perfluorohydrocarbyl group; and
$CrX_p$ is a chromium salt; X is a monoanion, and p is an integer from 2 to 6.

2. The catalyst system of claim 1, wherein the chromium salt is a chromium(III) carboxylate, a chromium(IIII) β-diketonate, or a chromium(III) halide.

3. The catalyst system of claim 1, wherein the chromium salt is chromium (III) chloride.

4. The catalyst system of claim 1, wherein the perfluorohydrocarbyl groups are independently selected from a $C_1$ to $C_{20}$ perfluorohydrocarbyl group, a $C_1$ to $C_{15}$ perfluorohydrocarbyl group, or a $C_1$ to $C_{10}$ perfluorohydrocarbyl group.

5. The catalyst system of claim 1, wherein $Rf^1$, $Rf^2$, $Rf^4$, and $Rf^5$ are independently selected from a mono-trifluoromethylphenyl group, a di-trifluoromethylphenyl group, or a tri-trifluoromethylphenyl group.

6. The catalyst system of claim 1, wherein $Rf^1$, $Rf^2$, $Rf^4$, and $Rf^5$ are independently selected from a $C_1$ to $C_{20}$ perfluoroalkyl group.

7. The catalyst system of claim 6, wherein the perfluoroalkyl groups are independently selected from a trifluoromethyl group, a 1,1-difluoroethyl group, or a pentafluoroethyl group.

8. The catalyst system of claim 1, wherein $Rf^1$, $Rf^2$, $Rf^4$, and $Rf^5$ are independently selected from a $C_6$ to $C_{20}$ perfluoroaryl group.

9. The catalyst system of claim 8, wherein $Rf^1$, $Rf^2$, $Rf^4$, and $Rf^5$ are independently selected from a $C_6$ to $C_{20}$ perfluorophenyl group.

10. The catalyst system of claim 9, wherein the perfluorophenyl groups are independently selected from a 2,4-diflurophenyl group, a 2,5-diflurophenyl group, a 3,5, difluorophenyl group, a 2,4,6-trifluorophenyl group, or a 2,3,4,5,6-pentafluorophenyl group.

11. The catalyst system of claim 1, wherein the $N^2$-phosphinylamidine chromium salt complex has the structure:

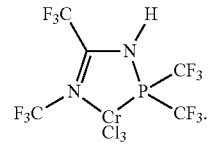

12. The catalyst system of claim 1, further comprising an organoaluminum compound.

13. The catalyst system of claim 12, wherein the organoaluminum compound comprises an aluminoxane.

14. The catalyst system of claim 13, wherein the aluminoxane comprises methylaluminoxane (MAO), a modified methylaluminoxane, ethylaluminoxane, n-propylaluminoxane, isopropylaluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, isopentylaluminoxane, neopentylaluminoxane, or mixtures thereof.

15. The catalyst system of claim 14, wherein the $N^2$-phosphinylamidine chromium salt complex has the structure:

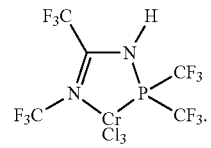

16. A process comprising:
a) contacting
i) ethylene,
ii) a catalyst system comprising an $N^2$-phosphinylamidine chromium salt complex having Structure PFHNPACr I:

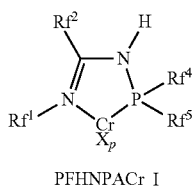

PFHNPACr I wherein each $Rf^1$, $Rf^2$, $Rf^4$, and $Rf^5$ are independently selected from a perfluorohydrocarbyl group and $CrX_p$ is a chromium salt; X is a monoanion and p is an integer from 2 to 6, and iii) optionally an organic reaction medium, and b) forming an oligomer product in a reaction zone.

17. The process of claim 16, wherein the $N^2$-phosphinylamidine chromium salt complex has the structure:

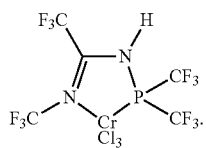

18. The process of claim 16, wherein the catalyst system further comprises an organoaluminum compound.

19. The process of claim 16, wherein the organoaluminum compound comprises an aluminoxane.

20. The catalyst system of claim 19, wherein the aluminoxane comprises methylaluminoxane (MAO), a modified methylaluminoxane, ethylaluminoxane, n-propylaluminoxane, isopropylaluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, isopentylaluminoxane, neopentylaluminoxane, or mixtures thereof.

21. The process of claim 20, wherein the $N^2$-phosphinylamidine chromium salt complex has the structure:

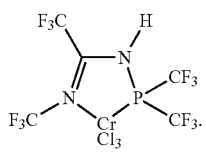

22. The process of claim 16, wherein a $C_6$ oligomer product has a 1-hexene content of at least 95 wt. %.

23. The process of claim 16, wherein a $C_a$ oligomer product has a 1-octene content of at least 95 wt. %.

24. The process of claim 16, wherein the oligomer product has a $C_8/C_6$ ratio is at least 1.5:1.

* * * * *